United States Patent [19]

Nakashima et al.

[11] Patent Number: 5,582,764
[45] Date of Patent: Dec. 10, 1996

[54] SILACYCLOHEXANE COMPOUND, A METHOD OF PREPARING IT AND A LIQUID CRYSTAL COMPOSITION CONTAINING IT

[75] Inventors: Mutsuo Nakashima; Takaaki Shimizu; Tsutomu Ogihara; Takeshi Kinsho; Tatsushi Kaneko, all of Kubiki-mura; Hideshi Kurihara, Kawasaki, all of Japan

[73] Assignee: Shin-Etsu Chemical Co., Ltd., Tokyo, Japan

[21] Appl. No.: 395,706

[22] Filed: Feb. 28, 1995

[30] Foreign Application Priority Data

| Mar. 1, 1994 | [JP] | Japan | 6-056565 |
| May 30, 1994 | [JP] | Japan | 6-139497 |
| Dec. 12, 1994 | [JP] | Japan | 6-332082 |

[51] Int. Cl.$^6$ .......................... C09K 19/34; C09K 19/30; C07F 7/08; G02F 1/13
[52] U.S. Cl. ................ 252/299.61; 252/299.63; 556/406; 349/182
[58] Field of Search ............... 252/299.66, 299.61, 252/299.63; 556/406; 359/103

[56] References Cited

U.S. PATENT DOCUMENTS

| 2,607,791 | 8/1952 | Goodwin ................. 556/406 X |
| 5,454,977 | 10/1995 | Shimizu et al. ............... 252/299.61 |

FOREIGN PATENT DOCUMENTS

| 0355008 | 8/1989 | European Pat. Off. . |
| 0630903 | 6/1994 | European Pat. Off. . |
| 0632044 | 1/1995 | European Pat. Off. . |

Primary Examiner—C. H. Kelly
Attorney, Agent, or Firm—Townsend & Banta

[57] ABSTRACT

A silacyclohexane compound represented by the following general formula (I).

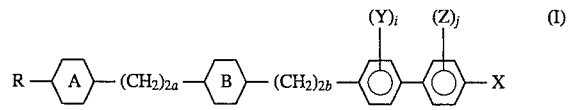

In this formula, R denotes a linear-chain alkyl group with a carbon number of 1–10, a fluoroalkyl group with a carbon number of 1–10 in which a fluorine atom(s) is substituted for one or two hydrogen atoms, an alkoxy group, a branched-chain alkyl group with a carbon number of 3–8, an alkoxyalkyl group with a carbon number of 2–7, or an alkenyl group with a carbon number of 2–8. a and b denote 0 or 1 and (a+b)=0 or 1; For

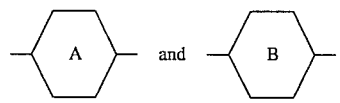

at least one of the two denotes a trans-1-sila-1,4-cyclohexylene or a trans-4-sila-1,4-cyclohexylene group whose silicon at position 1 or position 4 has a substitutional group(s) of H, F, Cl or $CH_3$. X denotes H, CN, F, Cl, $CF_3$, $CF_2Cl$, CHFCl, $OCF_3$, $OCF_2Cl$, OCHFCl, $OCHF_2$, R or OR. Y and Z denote F, Cl or $CH_3$. i and j denotes 0, 1 or 2.

33 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the Invention

This invention relates to a new silacyclohexane compound, a method of preparing it, and a liquid crystal composition which contains it, as well as a liquid crystal display element which contains said liquid crystal composition.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode), the PD mode (polymer dispersion mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required in all display methods. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are obtained by mixing several to more than ten liquid crystal compounds and latent liquid crystal compounds. Because of this, it is also important that components of a liquid crystal composition mix easily.

Of these components, the following compounds with the bicyclohexylbiphenyl structure have been known as compounds which have a particularly high $T_{NI}$ (nematic-isotropic transition temperature).

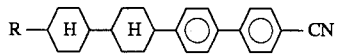
(See Japanese examined patent publication Tokko Sho 64-385.)

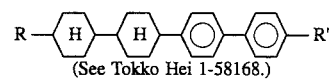
(See Tokko Hei 1-58168.)

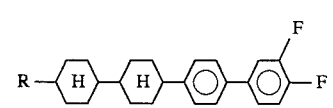
(See Japanese unexamined patent publication Tokkai Sho 63-287736.)

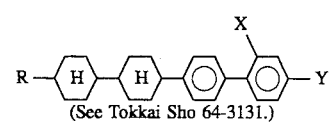
(See Tokkai Sho 64-3131.)

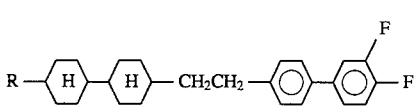
(See Tokko Hei 3-22855.)

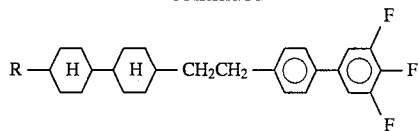
(See Tokkai Hei 2-233626.)

In recent years, along with the expansion of the applications of liquid crystal displays, the characteristics required of liquid crystal materials are becoming more and more advanced. In particular, there is a growing demand for materials with a nematic phase extended to a high temperature range which are to be used in conditions with a high ambient temperature such as automobile onboard use.

The nematic phase can be extended to a high temperature range by including a liquid crystal compound with a high $T_{NI}$ (nematic-isotropic transition temperature) as a component.

BRIEF SUMMARY OF THE INVENTION

The object of this invention is to provide a conventionally unknown and completely new liquid crystal compound containing silacyclohexane rings with a silicon atom(s) in its molecular structure, which has a high $T_{NI}$.

This invention provides a silacyclohexane compound represented by the following general formula (I).

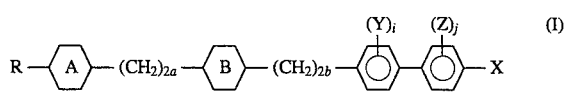

In this formula, R denotes a linear-chain alkyl group with a carbon number of 1–10, a fluoroalkyl group with a carbon number of 1–10 in which a fluorine atom(s) is substituted for one or two hydrogen atoms, an alkoxy group, a branched-chain alkyl group with a carbon number of 3–8, an alkoxyalkyl group with a carbon number of 2–7, or an alkenyl group with a carbon number of 2–8. a and b denote 0 or 1 and (a+b)=1 or 1. At least one of

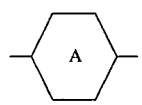

and

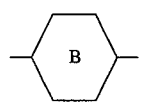

two denotes a trans-1-sila-1,4-cyclohexylene or a trans-4-sila-1,4-cyclohexylene group whose silicon at position 1 or position 4 has a substitutional group(s) of H, F, Cl or $CH_3$ and the other denotes a 1,4-silacyclohexylene group, a trans-1-sila-1,4-cyclohexylene or a trans-4-sila-1,4-cyclohexylene group whose silicon at position 1 or position 4 has a substitutional group of H, F, Cl or $CH_3$. X denotes H, CN, F, Cl, $CF_3$, $CF_2Cl$, $CHFCl$, $OCF_3$, $OCF_2Cl$, $OCHFCl$, $OCHF_2$, R or OR. Y and Z denote F, Cl or $CH_3$. i and j denotes 0, 1 or 2.

This invention also provides a silacyclohexane compound represented by the following general formula (II).

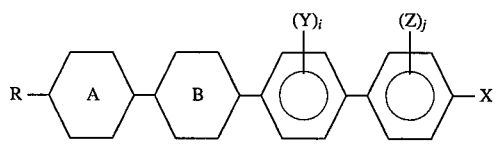 (II)

This invention also provides a silacyclohexane compound represented by the following general formula (III).

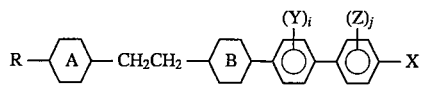 (III)

This invention also provides a silacyclohexane compound represented by the following general formula (IV).

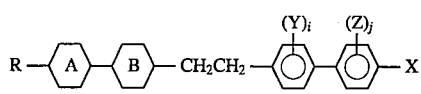 (IV)

This invention also provides a silacyclohexane compound represented by the following general formula (I) characterized by the use of a carbon-carbon bond formation reaction or a carbon-silicon bond formation reaction between an organometallic reagent R—M (M denotes MgP (P denotes a halogen atom), ZnP or Li) and

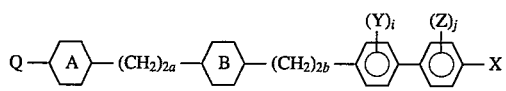

(Q denotes a halogen atom, or an alkoxy, methanesulfonyl, trifluoromethanesulfonyl or p-toluenesulfonyl group).

This invention also provides a silacyclohexane compound represented by the following general formula (I) characterized by the use of a carbon-carbon bond formation reaction or a carbon-silicon bond formation reaction between an organometallic reagent

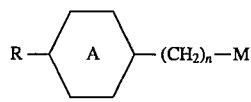

(M denotes MgP (P denotes a halogen atom), ZnP or Li) and

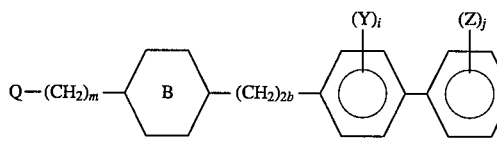

(Q denotes a halogen atom, or an alkoxy, methanesulfonyl, trifluoromethanesulfonyl or p-toluenesulfonyl group. (m and n are both the integers 0, 1 or 2, where m+n=2a).

This invention also provides a silacyclohexane compound represented by the following general formula (I) characterized by the use of a carbon-carbon bond formation reaction or a carbon-silicon bond formation reaction between an organometallic reagent

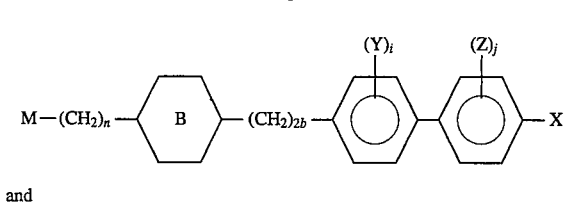

and

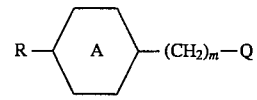

(m and n are both the integers 0, 1 or 2, where m+n=2a),

This invention also provides a silacyclohexane compound represented by the following general formula (I) characterized by the use of a carbon-carbon bond formation reaction or a carbon-silicon bond formation reaction between an organometallic reagent

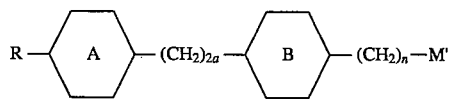

(M' denotes M or B(OR')$_2$ and R' denotes an alkyl group or a hydrogen atom) and

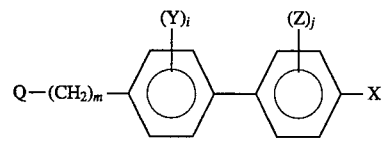

(m and n are both the integers 0, 1 or 2, where m+n=2b).

This invention also provides a silacyclohexane compound represented by the following general formula (I) characterized by the use of a carbon-carbon bond formation reaction or a carbon-silicon bond formation reaction between an organometallic reagent

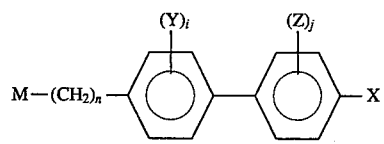

and

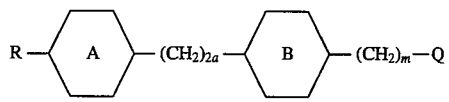

(w and n are both the integers 0, 1 or 2, where m+n=2b).

This invention also provides a silacyclohexane compound represented by the following general formula (I) characterized by the use of a carbon-carbon bond formation reaction or a carbon-silicon bond formation reaction between an organometallic reagent

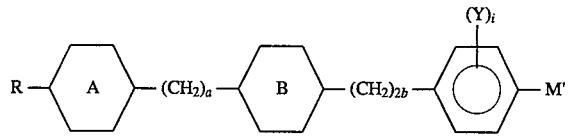

and

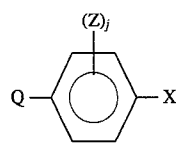

This invention also provides a silacyclohexane compound represented by the following general formula (I) characterized by the use of a carbon-carbon bond formation reaction or a carbon-silicon bond formation reaction between an organometallic reagent

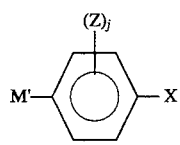

and

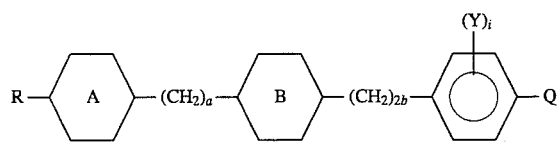

This invention also provides a method of preparing the silacyclohexane compound as represented by the general formula (II) characterized by the use of a carbon-carbon bond formation reaction or a carbon-silicon bond formation reaction between an organometallic reagent R—M (M denotes MgP (P denotes a halogen atom), ZnP or Li) and

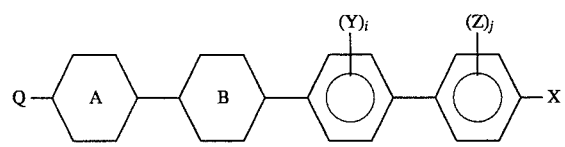

(Q denotes a halogen atom, or an alkoxy, methanesulfonyl, trifluoromethanesulfonyl or p-toluenesulfonyl group).

This invention also provides a method of preparing the silacyclohexane compound as represented by the general formula (II) characterized by the use of a carbon-carbon bond formation reaction or a carbon-silicon bond formation reaction between an organometallic reagent

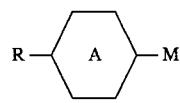

and

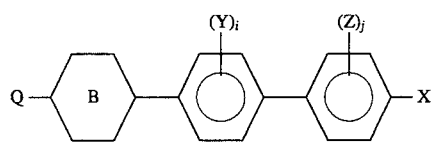

This invention also provides a method of preparing the silacyclohexane compound as represented by the general formula (II) characterized by the use of a carbon-carbon bond formation reaction or a carbon-silicon bond formation reaction between an organometallic reagent

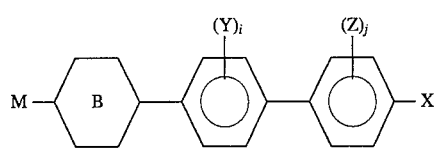

and

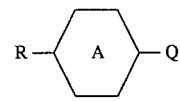

This invention also provides a method of preparing the silacyclohexane compound as represented by the general formula (II) characterized by the use of a carbon-carbon bond formation reaction or a carbon-silicon bond formation reaction between an organometallic reagent

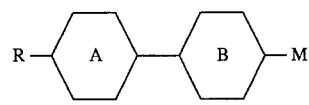

and

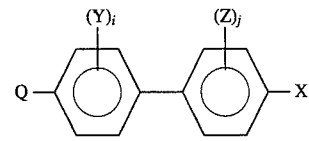

This invention also provides a method of preparing the silacyclohexane compound as represented by the general formula (II) characterized by the use of a carbon-carbon bond formation reaction or a carbon-silicon bond formation reaction between an organometallic reagent

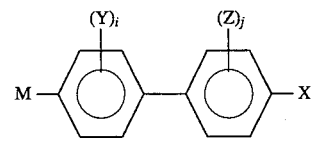

and

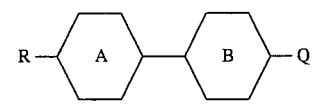

This invention also provides a method of preparing the silacyclohexane compound as represented by the general formula (II) characterized by the use of a carbon-carbon bond formation reaction or a carbon-silicon bond formation reaction between an organometallic reagent

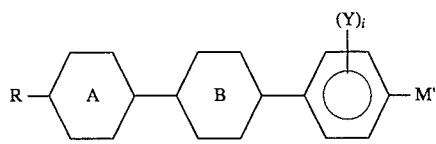

and

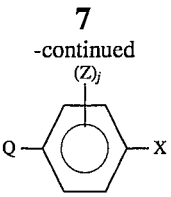

This invention also provides a method of preparing the silacyclohexane compound as represented by the general formula (II) characterized by the use of a carbon-carbon bond formation reaction or a carbon-silicon bond formation reaction between an organometallic reagent

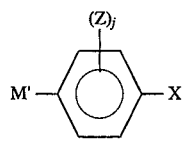

and

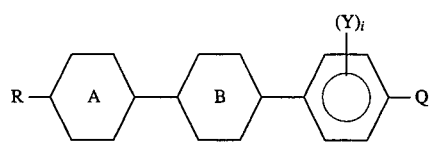

This invention also provides a method of preparing the silacyclohexane compound as represented by the general formula (IV) characterized by the use of a carbon-carbon bond formation reaction or a carbon-silicon bond formation reaction between an organometallic reagent R—M (M denotes MgP (P denotes a halogen atom), ZnP or Li) and

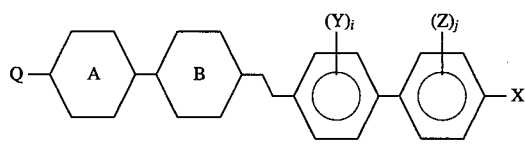

(Q denotes a halogen atom, or an alkoxy, methanesulfonyl, benzenesulfonyl, p-toluenesulfonyl or trifluoromethanesulfonyl group).

This invention also provides a method of preparing the silacyclohexane compound as represented by the general formula characterized by the use of a carbon-carbon bond formation reaction or a carbon-silicon bond formation reaction between an organometallic reagent

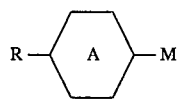

and

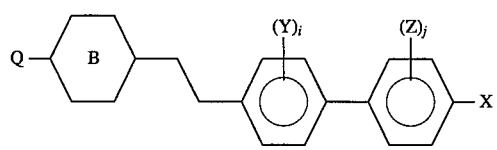

This invention also provides a method of preparing the silacyclohexane compound as represented by the general formula (IV) characterized by the use of a carbon-carbon bond formation reaction or a carbon-silicon bond formation reaction between an organometallic reagent

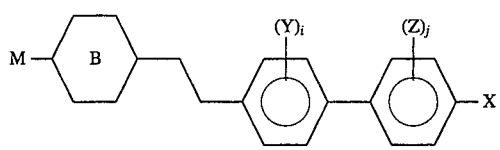

and

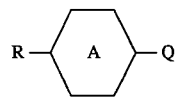

This invention also provides a method of preparing the silacyclohexane compound as represented by the general formula (IV) characterized by the use of a carbon-carbon bond formation reaction between an organometallic reagent

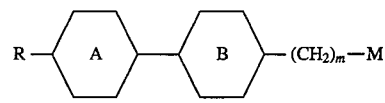

and

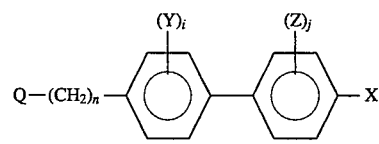

(m and n are both the integers 0, 1 or 2, where m+n=2).

This invention also provides a method of preparing the silacyclohexane compound as represented by the general formula (IV) characterized by the use of a carbon-carbon bond formation reaction or a carbon-silicon bond formation reaction between an organometallic reagent

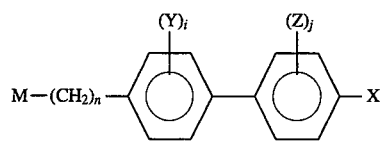

and

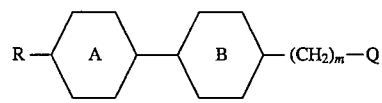

This invention also provides a method of preparing the silacyclohexane compound as represented by the general formula (IV) characterized by the use of a carbon-carbon bond formation reaction between an organometallic reagent

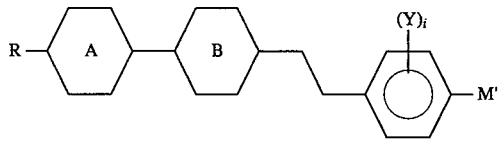

(M' denotes M or B(OR')$_2$ (R' denotes an alkyl group or a H atom)) and

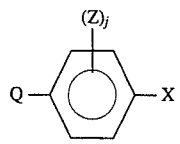

This invention also provides a method of preparing the silacyclohexane compound as represented by the general formula (IV) characterized by the use of a carbon-carbon bond formation reaction between an organometallic reagent

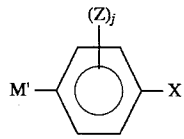

and

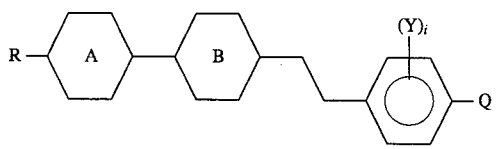

This invention also provides a method of preparing the silacyclohexane compound as represented by the general formula (III) characterized by the use of a reaction between an organometallic reagent R—M (M denotes MgP (P denotes a halogen atom), ZnP or Li) and

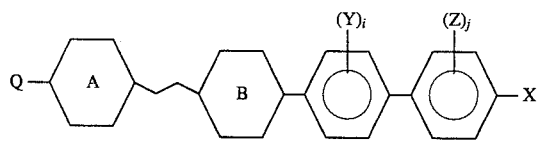

(Q denotes a halogen atom, or an alkoxy, methanesulfonyl, benzenesulfonyl or p-toluenesulfonyl group).

This invention also provides a method of preparing the silacyclohexane compound as represented by the general formula (III) characterized by the use of a reaction between an organometallic reagent

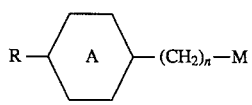

and

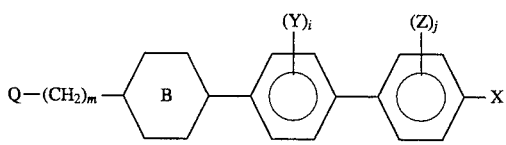

(n and m are both the integers 0, 1 or 2, where n+m=2).

This invention also provides a method of preparing the silacyclohexane compound as represented by the general formula (III) characterized by the use of a reaction between an organometallic reagent

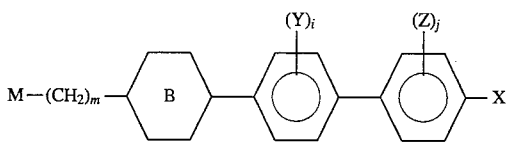

and

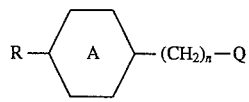

This invention also provides a method of preparing the silacyclohexane compound as represented by the general formula (III) characterized by the use of a reaction between an organometallic reagent

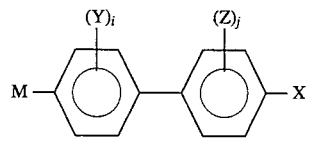

and

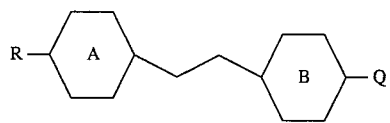

This invention also provides a method of preparing the silacyclohexane compound as represented by the general formula (III) characterized by the use of a reaction between an organometallic reagent

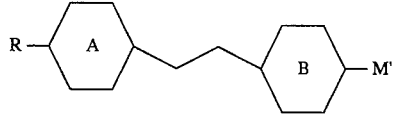

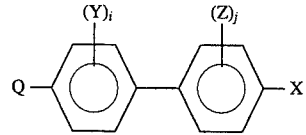

(M' denotes MgP (P denotes a halogen atom), ZnP or B(Or'), (R' is H or an alkyl group)) and

This invention also provides a method of preparing the silacyclohexane compound as represented by the general formula (III) characterized by the use of a reaction between an organometallic reagent

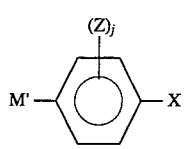

and

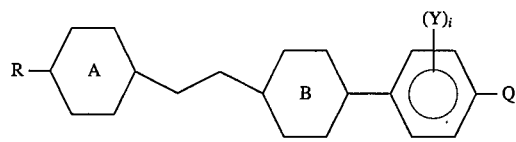

Furthermore, this invention provides a liquid crystal composition characterized by containing the silacyclohexane compound represented by the general formula (I) and a liquid crystal display element which contains said liquid crystal composition.

DETAILED DESCRIPTION

This invention is described in detail below. First, specific examples of the silacyclohexane compound represented by the general formula (I) and more concretely represented by the general formulas (II) to (IV) are described.

Examples of the ring structure of the silacyclohexane compound of this invention are shown below.

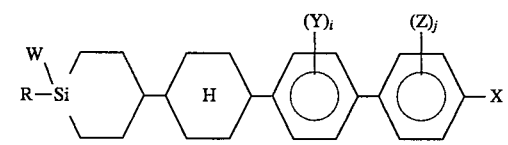

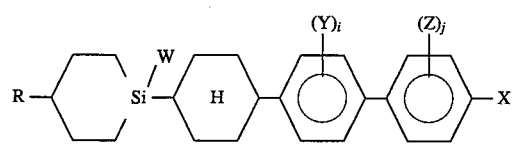

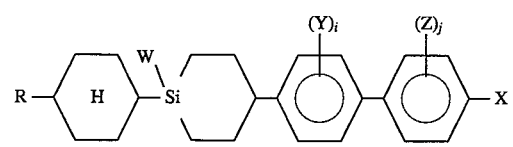

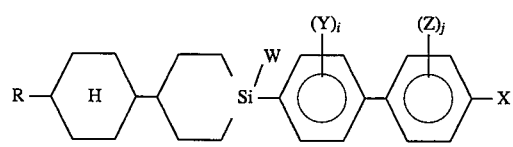

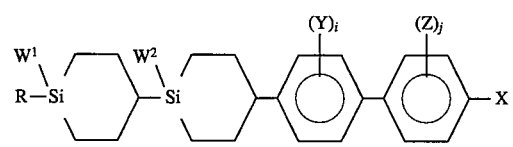

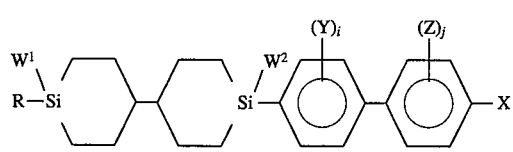

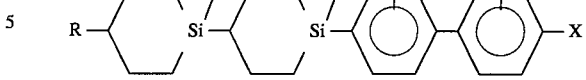

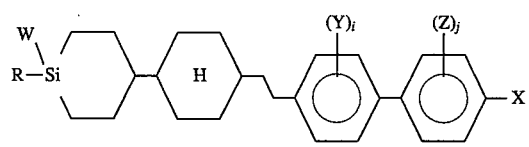

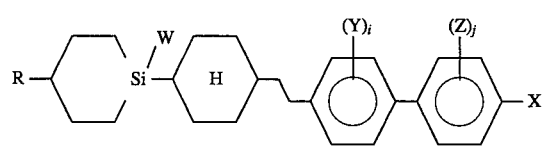

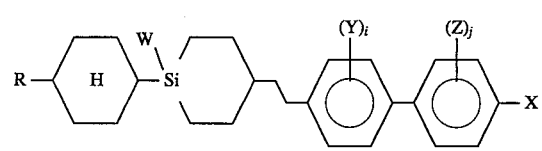

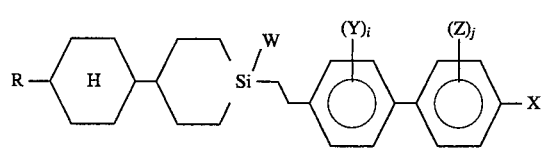

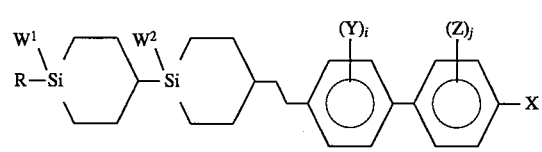

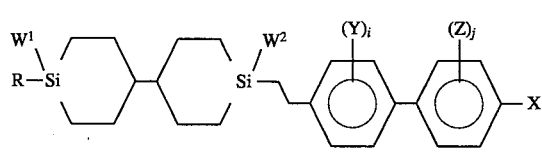

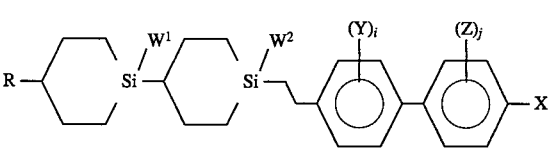

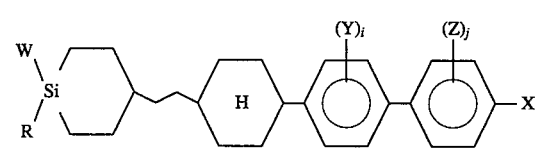

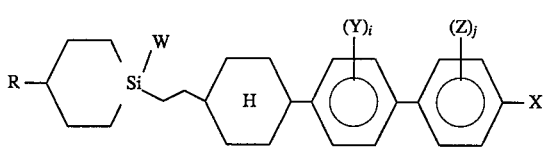

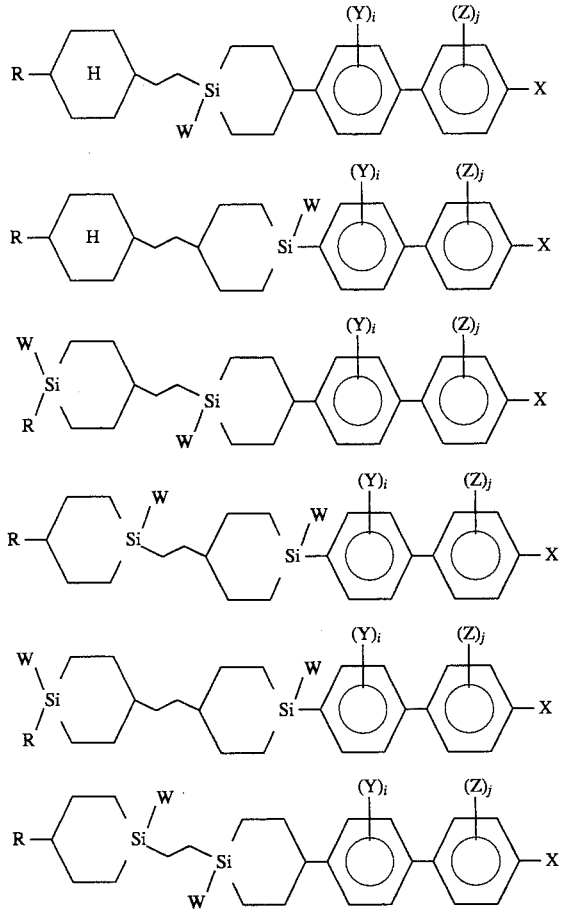

In the chemical formulas above, R, W, $W^1$ and $W^2$ denote the following.

R denotes one of (a) through (f) shown below.

(a) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (b) A mono- or di-fluoroalkyl group with a carbon number of 1–10, i.e. fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl. 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl or 10,10-difluorodecyl group (c) A linear-chain alkoxy group with a carbon number of 1–10, i.e. a methoxy, ethoxy, n-propoxy, n-butoxy, n-pentoxy, n-hexyloxy, n-heptyloxy, n-octyloxy, n-nonyloxy or n-decyloxy group (d) A branched-chain alkyl group with a carbon number of 3–8, i.e. an isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group (e) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl or ethoxypentyl group (f) An alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group W, $W^1$ and $W^2$ independently denote H, F, Cl or $CH_3$.

X denotes H, CN, F, Cl, $CF_3$, $CF_2Cl$, $CHFCl$, $OCF_3$, $OCF_2Cl$, $OCHFCl$, $OCHF_2$ or one of (g) through (i) shown below.

(g) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (h) A linear-chain alkoxy group with a carbon number of 1–10, i.e. a methoxy, ethoxy, n-propoxy, n-butoxy, n-pentoxy, n-hexyloxy, n-heptyloxy, n-octyloxy, n-nonyloxy or n-decyloxy group (i) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl, ethoxypentyl or methoxyhexyl group Specific examples of the partial structure

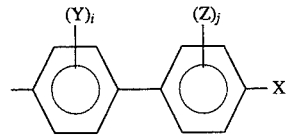

follow.

-continued
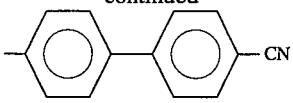
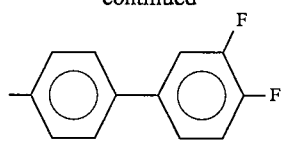
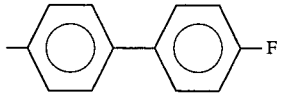
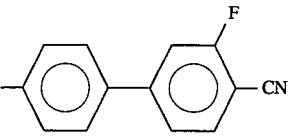
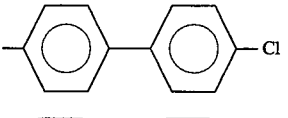
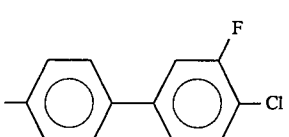
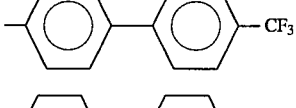
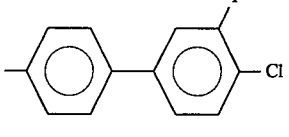
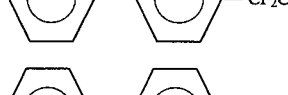
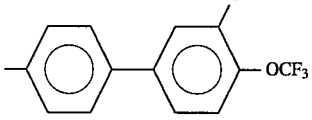
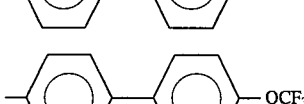 (1 ≦ k ≦ 10)
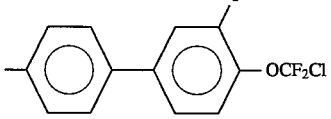 (1 ≦ l ≦ 10)
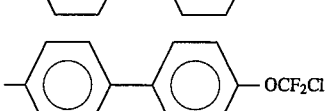 (2 ≦ l+k ≦ 7)
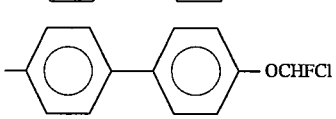
-continued
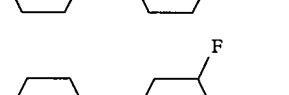
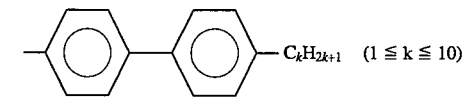
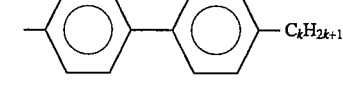
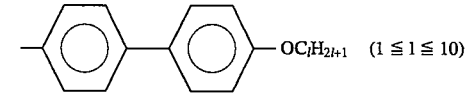
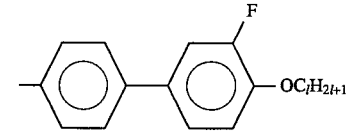
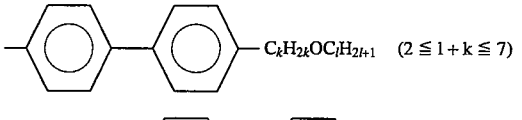
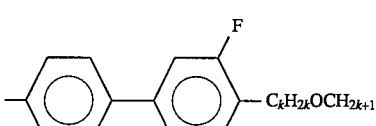
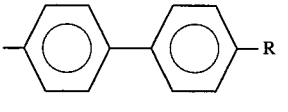
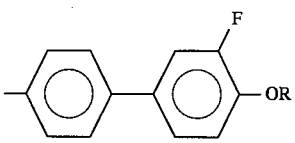
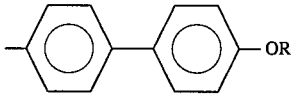

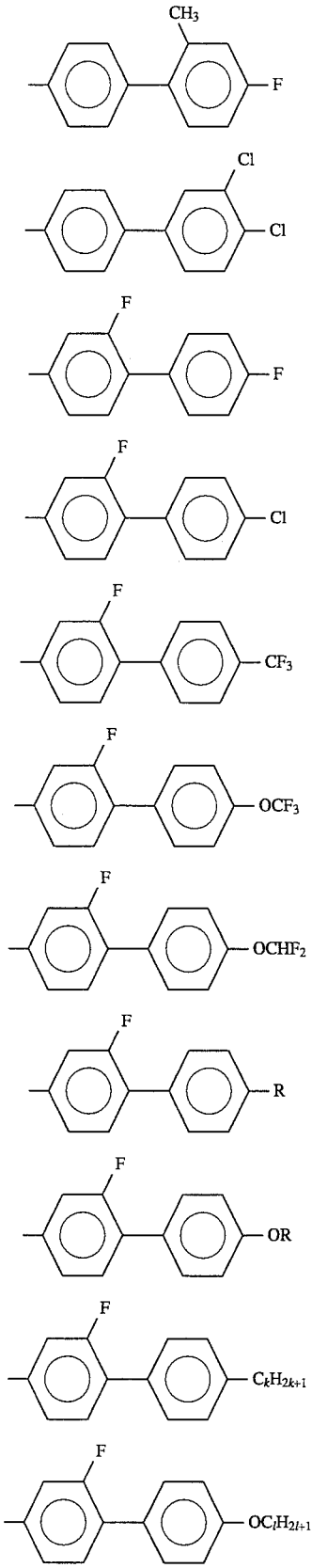
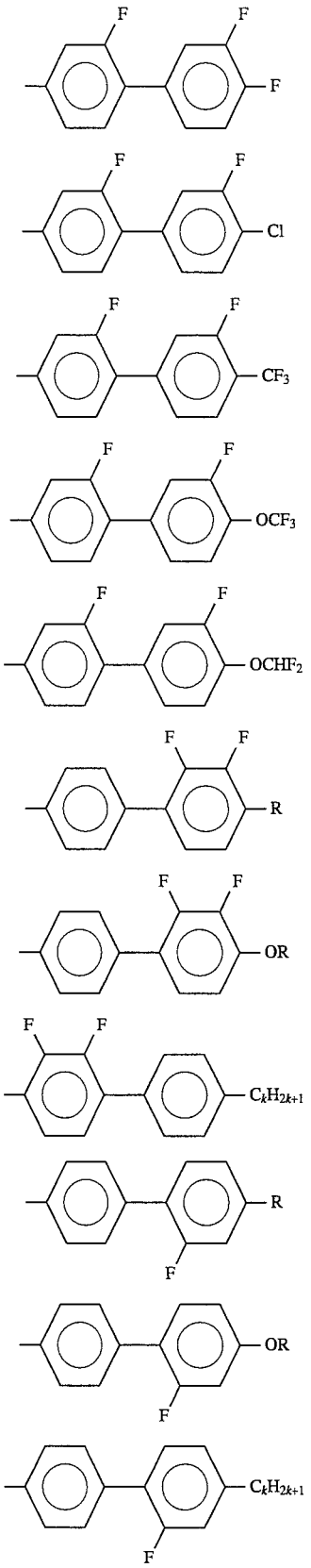

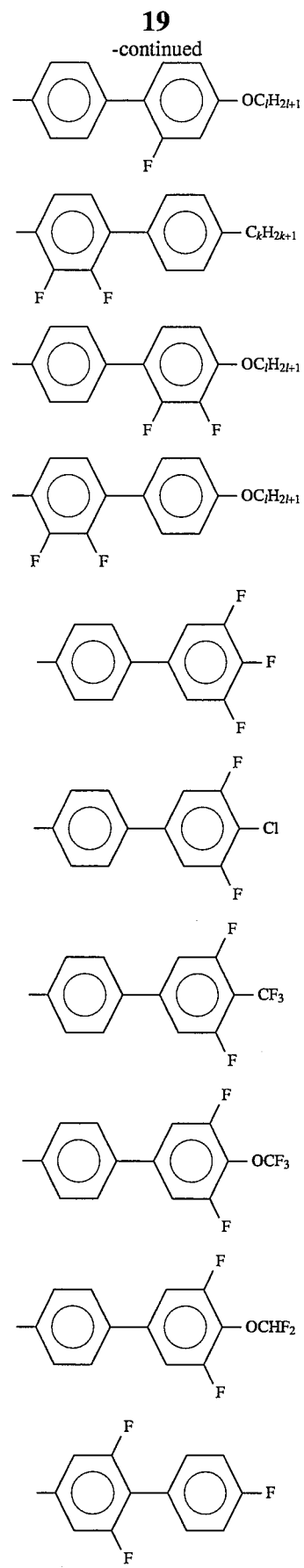
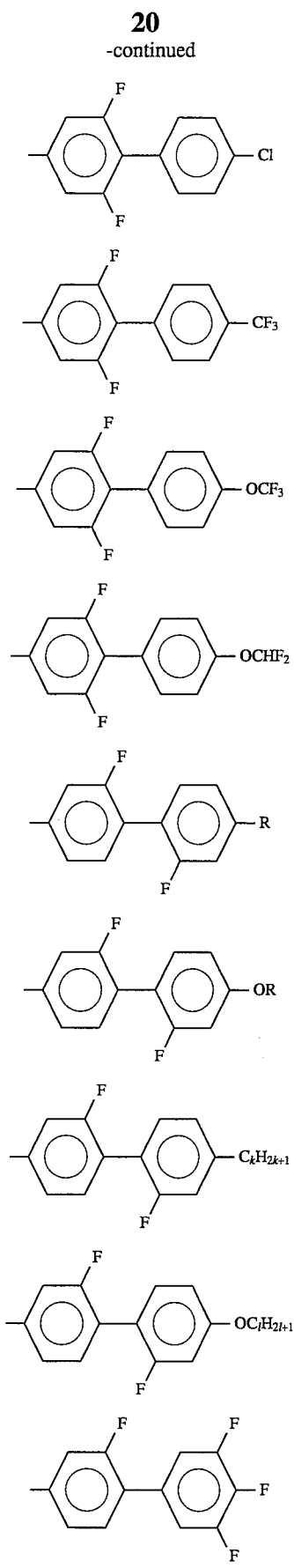

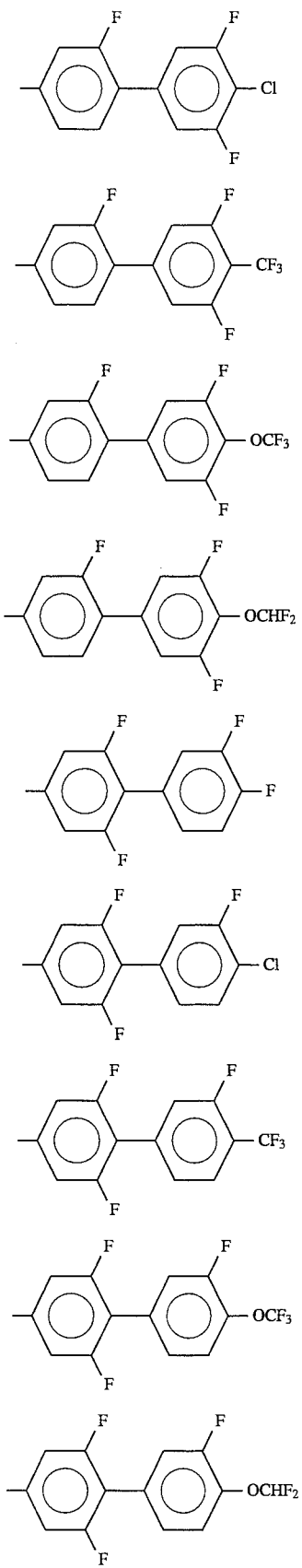
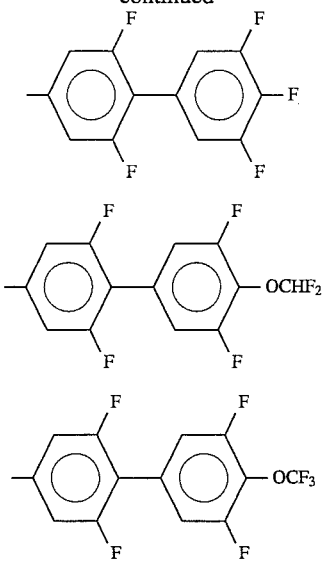
Of these, the following are preferable for practical use. For the ring structure,
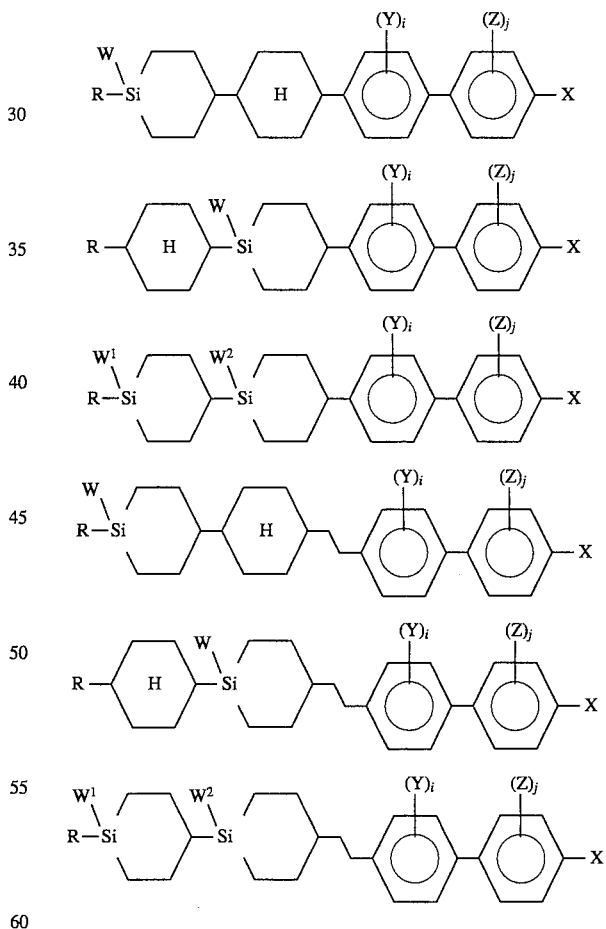
are preferable.
For R, the following groups listed in (j) through (n) are preferable.
(j) A linear-chain alkyl or alkoxy group with a carbon number of 3–7, i.e. a n-propyl, n-butyl, n-pentyl, n-hexyl, n-heptyl, n-propoxy, n-butoxy, n-pentoxy, n-hexyloxy, n-heptyloxy group (k) Some mono- or di-fluoroalkyl groups including 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl groups (l) Some branched-chain alkyl groups including isopropyl, 1-methylpropyl, 2-methylpropyl, 1-methylbutyl, 2-methylbutyl, 3-methylbutyl, 1-methylpentyl, 2-methylpentyl and 2-ethylhexyl groups (m) An alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group (n) Some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups H, F and $CH_3$ groups are desirable for W, $W^1$ and $W^2$ in practical use.

For the partial structure

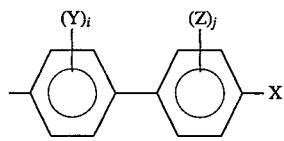

the following are preferable.

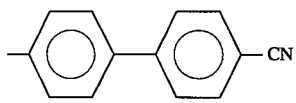

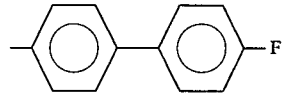

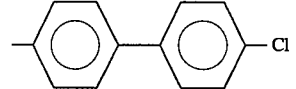

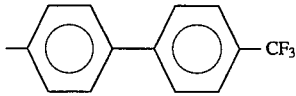

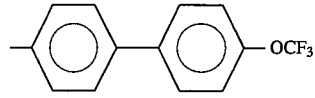

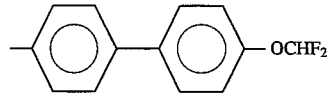

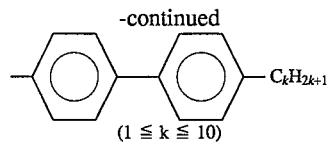
$(1 \leq k \leq 10)$

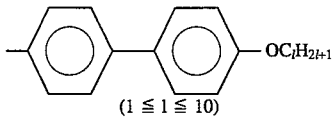
$(1 \leq l \leq 10)$

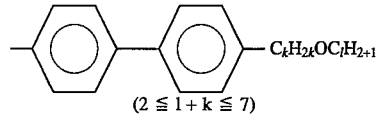
$(2 \leq l+k \leq 7)$

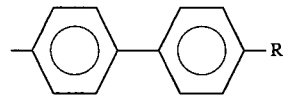

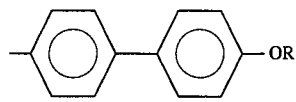

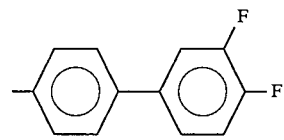

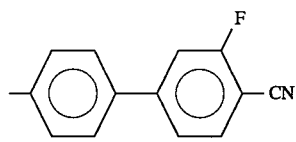

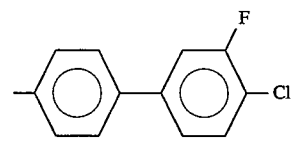

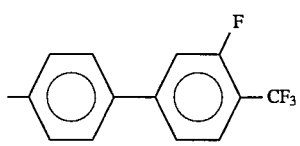

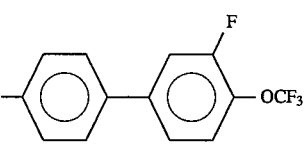

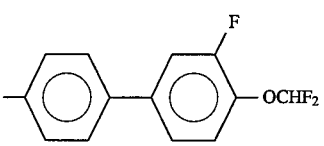

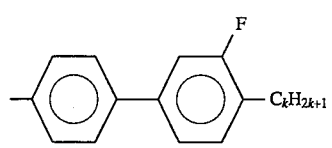

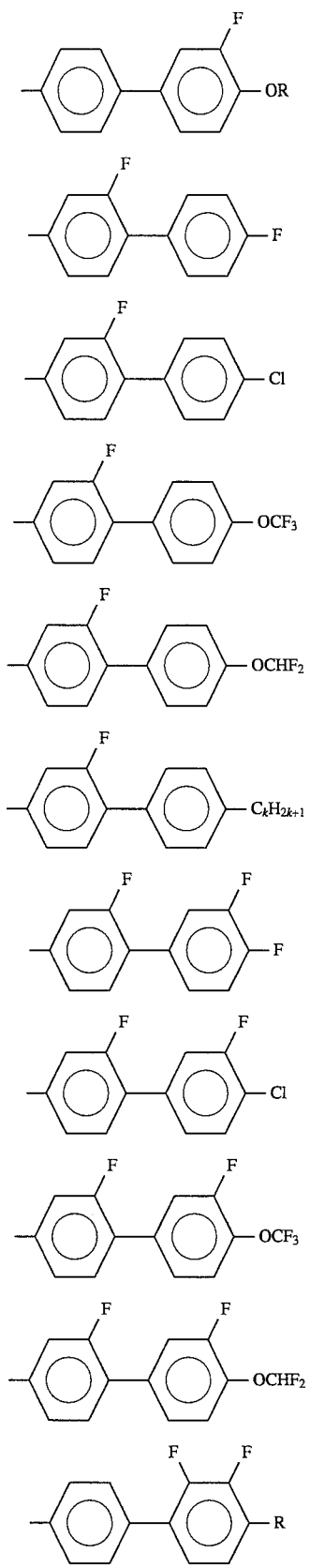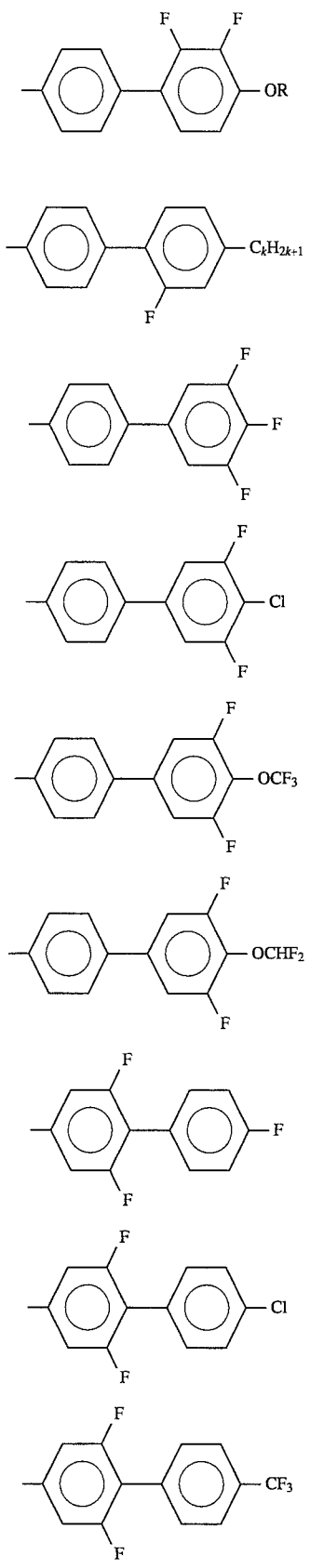

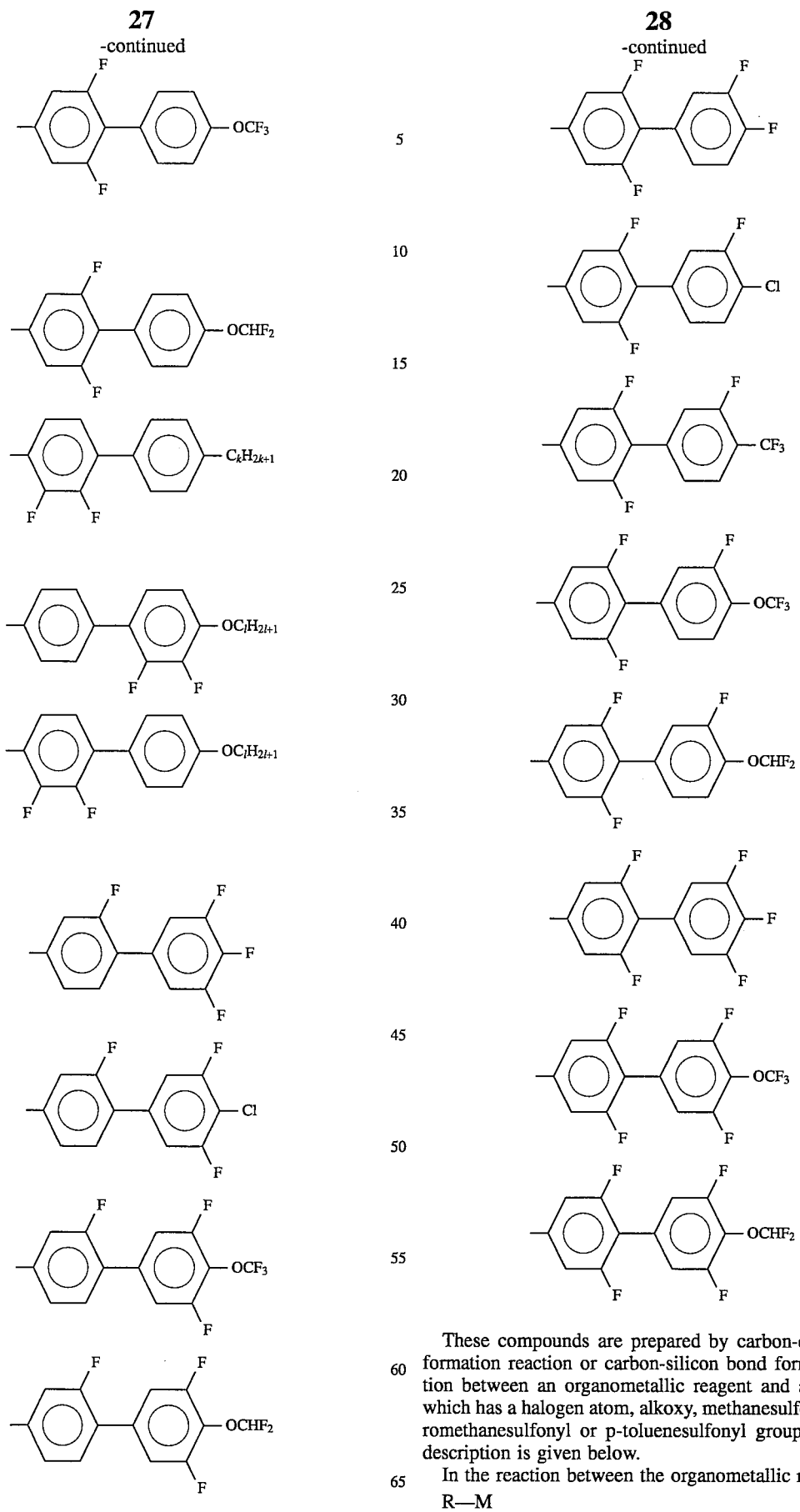

These compounds are prepared by carbon-carbon bond formation reaction or carbon-silicon bond formation reaction between an organometallic reagent and a compound which has a halogen atom, alkoxy, methanesulfonyl, trifluoromethanesulfonyl or p-toluenesulfonyl group. A detailed description is given below.

In the reaction between the organometallic reagent
R—M (M denotes MgP (P denotes a halogen atom), ZnP or Li) and

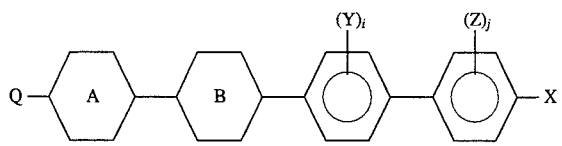

(Q denotes a halogen atom, or an alkoxy, methanesulfonyl, trifluoromethanesulfonyl or p-toluenesulfonyl group), when

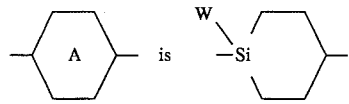

(W denotes H, F, Cl or $CH_3$), Q is a halogen atom or an alkoxy group, for example. Particularly, if Q is a Cl or Br atom, or an $OCH_3$ or $OCH_2CH_3$ group, then the carbon-silicon bond formation reaction proceeds easily and gives a high yield of the target product.

When

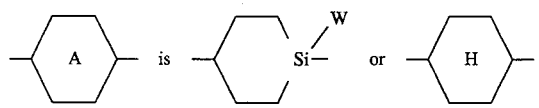

this carbon-carbon bond formation reaction is carried out in the presence of a catalytic amount of copper salt. In this case, Q is a halogen atom or a methanesulfonyl, trifluoromethanesulfonyl or p-toluenesulfonyl group, for example. It is particularly preferable if Q is Br or I because then the target product can be obtained with a high yield.

In the reaction between the organometallic reagent

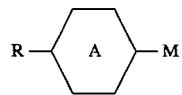

and

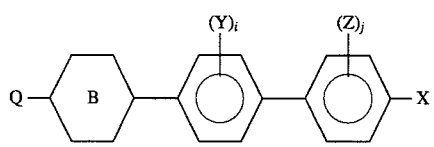

when

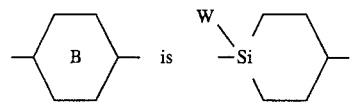

(W denotes H, F, Cl or $CH_3$), Q is a halogen atom or an alkoxy group, for example. Particularly, if Q is a Cl or Br atom, or an $OCH_3$ or $OCH_2CH_3$ group, then the carbon-silicon bond formation reaction proceeds easily and gives a high yield of the target product.

When

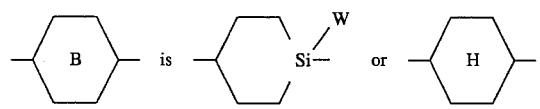

this carbon-carbon bond formation reaction is carried out in the presence of a catalytic amount of copper salt. In this case, Q is a halogen atom or a methanesulfonyl, trifluoromethanesulfonyl or p-toluenesulfonyl group, for example. It is particularly preferable if Q is Br or I because then the target product can be obtained with a high yield.

In the reaction between the organometallic reagent

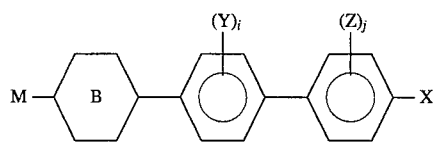

and

when

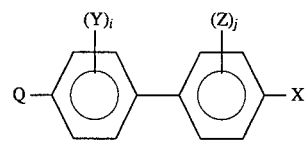

(W denotes H, F, Cl or $CH_3$), Q is a halogen atom or an alkoxy group, for example. Particularly, if Q is a Cl or Br atom, or an $OCH_3$ or $OCH_2CH_3$ group, then the carbon-silicon bond formation reaction proceeds easily and gives a high yield of the target product.

When

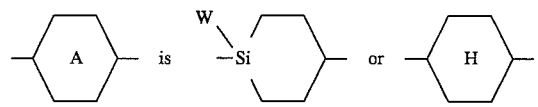

this carbon-carbon bond formation reaction is carried out in the presence of a catalytic amount of copper salt. In this case, Q is a halogen atom or a methanesulfonyl, trifluoromethanesulfonyl or p-toluenesulfonyl group, for example. It is particularly preferable if Q is Br or I because then the target product can be obtained with a high yield.

The carbon-carbon bond formation reaction between the organometallic reagent and is carried out in the presence of a transition metal catalyst. For Q, a halogen atom or a methanesulfonyl, trifluoromethanesulfonyl or p-toluenesulfonyl group can be used.

For the catalyst, palladium and nickel compounds are preferable.

Examples of the palladium catalysts are zero-valent palladium compounds such as tetrakis (triphenylphosphine) palladium (0) and di[1,2-bis(diphenylphosphino)ethane]palladium (0), or divalent palladium compounds such as palladium acetate and palladium chloride and complex compounds composed of these and a ligand(s), as well as a combination of these divalent palladium compounds and a reducing agent.

Examples of the nickel catalysts are divalent nickel compounds such as 1,2-bis(diphenylphosphino)ethane nickel (II) chloride, 1,3-bis(diphenylphosphino)propane nickel (II) chloride, and bis(triphenylphosphine)nickel (II) chloride, and zero-valent nickel compounds such as tetrakis (triphenylphosphine) nickel (0).

In the reaction between the organometallic reagent

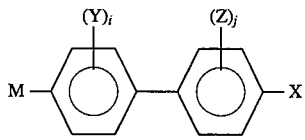

and

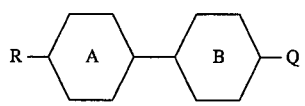

when

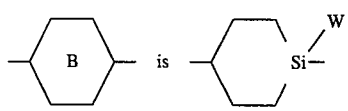

(W denotes H, F, Cl or CH$_3$), Q is a halogen atom or an alkoxy group, for example. Particularly, if Q is a Cl or Br atom, or an OCH$_3$ or OCH$_2$CH$_3$ group, then the carbon-silicon bond formation reaction proceeds easily and gives a high yield of the target product.

When

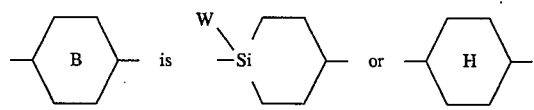

this carbon-carbon bond formation reaction is carried out in the presence of a catalytic amount of copper salt. In this case. Q is a halogen atom or a methanesulfonyl. trifluoromethanesulfonyl or p-toluenesulfonyl group, for example. It is particularly preferable if Q is Br or I because then the target product can be obtained with a high yield.

For the reaction between the organometallic reagent

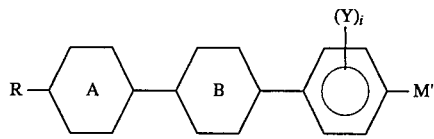

and

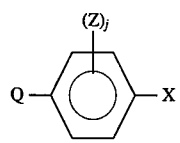

or the reaction between the organometallic reagent

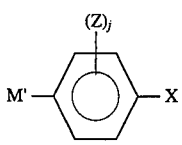

and

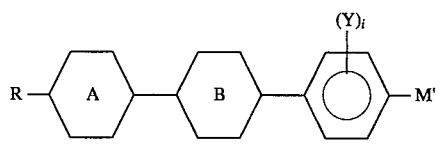

these carbon-carbon bond formation reactions are carried out in the presence of a transition metal catalyst M' denotes M or B(OR')$_2$ and R' denotes an alkyl group or a hydrogen atom. For Q, a halogen atom or a methanesulfonyl, trifluoromethanesulfonyl or p-toluenesulfonyl group can be used.

In the reaction between the organometallic reagent

R—M and

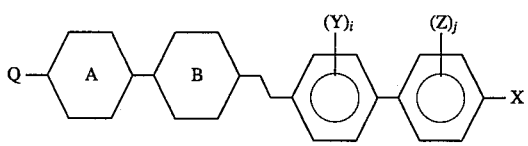

(M denotes MgP (P denotes a halogen atom), ZnP or Li, and Q denotes a halogen atom, or an alkoxy, methanesulfonyl, p-toluenesulfonyl or trifluoromethanesulfonyl group), when

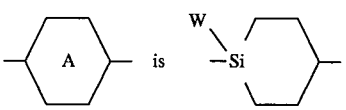

(W denotes H, F, Cl or CH$_3$), Q is a halogen atom or an alkoxy group, for example. It is particularly preferable if Q is a Cl or Br atom, or an OCH$_3$ or OCH$_2$CH$_3$ group because then the carbon-silicon bond formation reaction proceeds easily and gives a high yield of the target product.

When

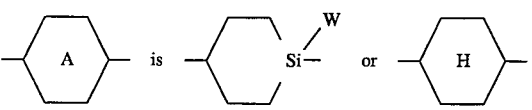

this carbon-carbon bond formation reaction is carried out in the presence of a catalytic amount of copper salt. In this case, Q is a halogen atom or a sulfonyl group, for example. It is particularly preferable if Q is Br, I or a trifluoromethanesulfonyl group because then the target product can be obtained with a high yield.

In the reaction between the organometallic reagent

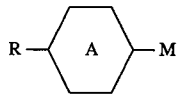

and

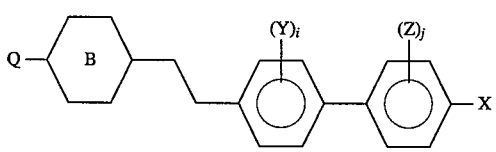

when

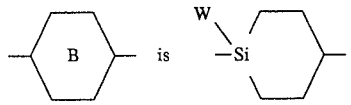

Q is a halogen atom or an alkoxy group, for example. It is particularly preferable if Q is a Cl or Br atom, or an OCH$_3$ or OCH$_2$CH$_3$ group, because then the carbon-silicon bond formation reaction proceeds easily and gives a high yield of the target product.

When

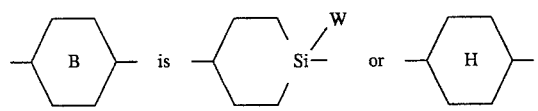

this carbon-carbon bond formation reaction is carried out in the presence of a catalytic amount of copper salt. In this case, Q is a halogen atom or a sulfonyl group, for example. It is particularly preferable if Q is Br, I or a trifluoromethanesulfonyl group because then the target product can be obtained with a high yield.

In the reaction between the organometallic reagent

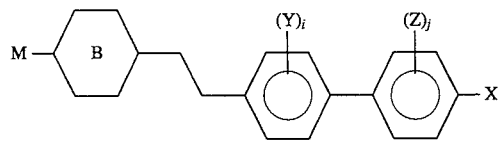

and

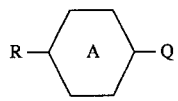

when

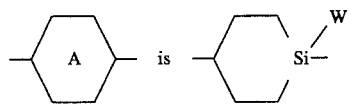

Q is a halogen atom or an alkoxy group, for example. It is particularly preferable if Q is a Cl or Br atom, or an OCH$_3$ or OCH$_2$CH$_3$ group because then the carbon-silicon bond formation reaction proceeds easily and gives a high yield of the target product.

When

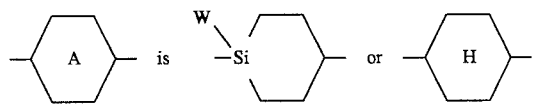

this carbon-carbon bond formation reaction is carried out in the presence of a catalytic amount of copper salt. In this case, Q is a halogen atom or a sulfonyl group, for example. It is particularly preferable if Q is Br, I or a p-toluenesulfonyl group because then the target product can be obtained with a high yield.

In the reaction between the organometallic reagent

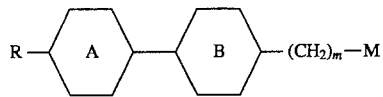

and

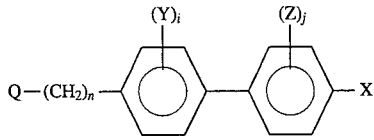

(m and n are both the integers 0, 1 or 2, where n+m=2), when m=0 or 1 in

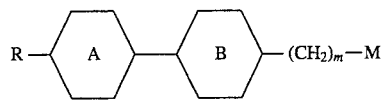

this carbon-carbon bond formation reaction is carried out in the presence of a catalytic amount of copper salt. In this case, Q is a halogen atom or a sulfonyl group, for example. It is particularly preferable if Q is Br, I or a trifluoromethanesulfonyl group because then the target product can be obtained with a high yield.

When m=2 in

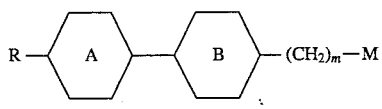

this carbon-carbon bond formation reaction is carried out in the presence of a transition metal catalyst.

For the transition metal catalyst, palladium and nickel compounds are preferable.

Examples of the palladium catalysts are zero-valent palladium compounds such as tetrakis (triphenylphosphine) palladium (0) and di[1,2-bis(diphenylphosphino)ethane]palladium (0), or divalent palladium compounds such as palladium acetate and palladium chloride and complex compounds composed of these and a ligand(s), as well as a combination of these divalent palladium compounds and a reducing agent.

Examples of the nickel catalysts are divalent nickel compounds such as 1,2-bis(diphenylphosphino)ethane nickel (II) chloride, 1,8-bis(diphenylphosphino)propane nickel chloride, and bis(triphenylphosphine)nickel (II) chloride, and zero-valent nickel compounds such as tetrakis (triphenylphosphine) nickel (0).

Q is a halogen atom or a sulfonyl group, for example. It is particularly preferable if Q is Cl, Br or I because then the target product can be obtained with a high yield.

In the reaction between the organometallic reagent

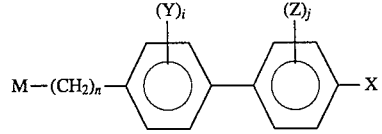

and

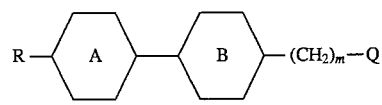

when is

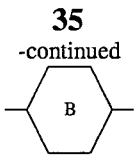

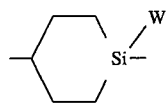

and m = 0 or 1 in

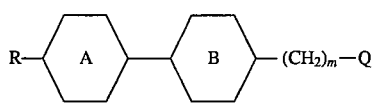

Q is a halogen atom or an alkoxy group, for example. It is particularly preferable if Q is a Cl or Br atom, or an OCH₃ or OCH₂CH₃ group because then the carbon-silicon bond formation reaction proceeds easily and gives a high yield of the target product. When

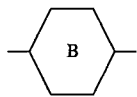

is

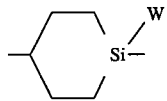

and m = 1 or 2 in

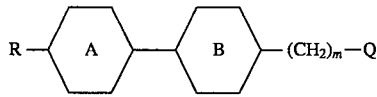

or

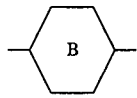

is

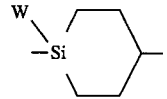

or

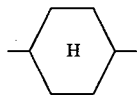

this carbon-carbon bond formation reaction is carried out in the presence of a catalytic amount of copper salt. In this case, Q is a halogen atom or a sulfonyl group, for example. It is particularly preferable if Q is Br, I or a trifluoromethanesulfonyl group because then the target product can be obtained with a high yield.

The carbon-carbon bond formation reaction between the organometallic reagent

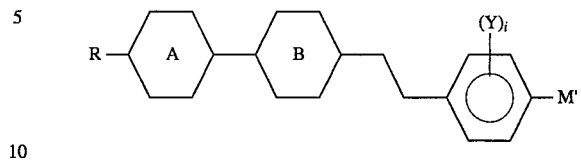

(M' denotes M or B(OR')₂ and R' denotes an alkyl group or a hydrogen atom) and

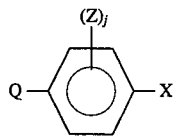

is carried out in the presence of a transition metal catalyst.

For the transition metal catalyst, palladium and nickel compounds are preferable.

Examples of the palladium catalysts are zero-valent palladium compounds such as tetrakis (triphenylphosphine) palladium (0) and di[1,2-bis(diphenylphosphino)ethane]palladium (0), or divalent palladium compounds such as palladium acetate and palladium chloride and complex compounds composed of these and a ligand(s), as well as a combination of these divalent palladium compounds and a reducing agent.

Examples of the nickel catalysts are divalent nickel compounds such as 1,2-bis(diphenylphosphino)ethane nickel (II) chloride, 1,3-bis(diphenylphosphino)propane nickel (II) chloride, and bis(triphenylphosphine)nickel (II) chloride, and zero-valent nickel compounds such as tetrakis (triphenylphosphine) nickel (0).

For the organometallic reagent, a Grignard's reagent, organozinc reagent or organoboric acid reagent, i.e. when M' is MgP, ZnP or B(OR')₂, gives preferable results.

When M' is B (OR')₂, the reaction should preferably be carried out in the presence of a base. For the base, for example, inorganic bases such as sodium carbonate, sodium bicarbonate, potassium carbonate, sodium hydroxide and potassium hydroxide, and organic bases such as triethylamine, dimethylaniline and tributylamine can be used.

In the reaction between an organometallic reagent

R—M (M denotes MgP (P denotes a halogen atom), ZnP or Li) and

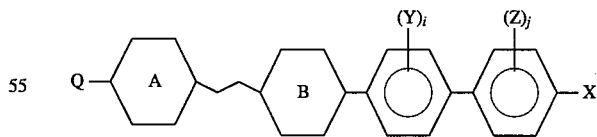

(Q denotes a halogen atom, or an alkoxy, methanesulfonyl, benzenesulfonyl or p-toluenesulfonyl group), when

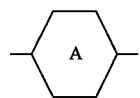

is

-continued

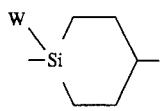

(W denotes H, F, Cl or CH$_3$), Q is a halogen atom or an alkoxy group, for example. Particularly, if Q is a Cl or Br atom, or an OCH$_3$ or OCH$_2$CH$_3$ group, then the carbon-silicon bond formation reaction proceeds easily and gives a high yield of the target product.

When

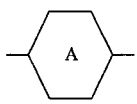

is

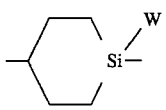

or

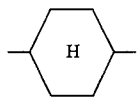

this carbon-carbon bond formation reaction is carried out in the presence of a catalytic amount of copper salt. In this case, Q is a halogen atom or a methanesulfonyl, benzenesulfonyl or p-toluenesulfonyl group, for example. It is particularly preferable if Q is Br or I because then the target product can be obtained with a high yield.

For the reaction between the organometallic reagent

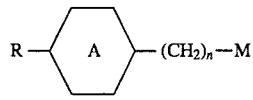

and

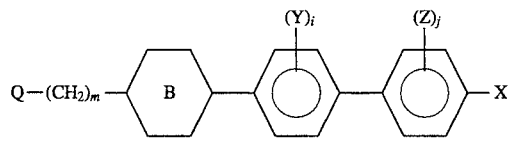

or the reaction between the organometallic reagent

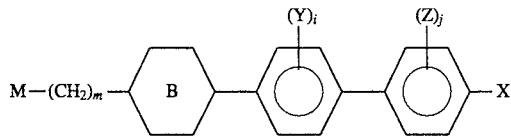

and

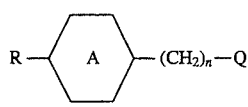

these carbon-carbon bond formation reactions are carried out in the presence of a catalytic amount of copper salt. In this case, Q is a halogen atom or a methanesulfonyl, benzenesulfonyl or p-toluenesulfonyl group, for example. It is particularly preferable if Q is Br, I or a p-toluenesulfonyl group because then the target product can be obtained with a high yield.

In the reaction between the organometallic reagent

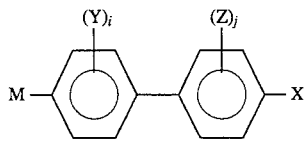

and

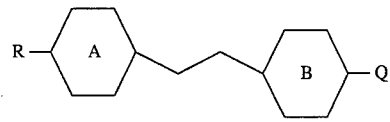

when

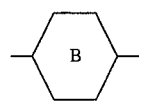

is

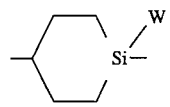

(W denotes H, F, Cl or CH$_3$), Q is a halogen atom or an alkoxy group, for example. Particularly, if Q is a Cl or Br atom, or an OCH$_3$ or OCH$_2$CH$_3$ group, then the carbon-silicon bond formation reaction proceeds easily and gives a high yield of the target product.

When

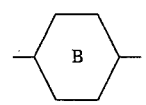

is

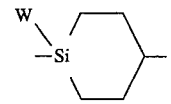

or

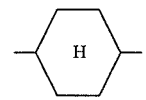

this carbon-carbon bond formation reaction is carried out in the presence of a catalytic amount of copper salt. In this case, Q is a halogen atom or a methanesulfonyl, benzenesulfonyl or p-toluenesulfonyl group, for example. It is particularly preferable if Q is Br, I or a p-toluenesulfonyl group because then the target product can be obtained with a high yield.

The reaction between the organometallic reagent

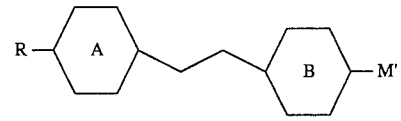

(M' denotes MgP (P denotes a halogen atom), ZnP, Li or B(OR')$_2$ (Y denotes H or an alkyl group)) and

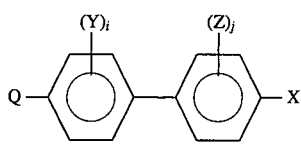

and the reaction between the organometallic reagent

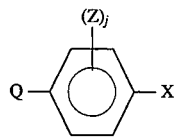

and

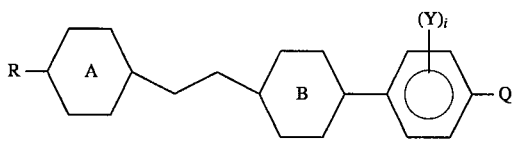

are carried out in the presence of a transition metal catalyst.

Following a conventional after treatment and purification procedure, the target silacyclohexane compound can be obtained from the products of the reactions as described above. The compound produced here may be a mixture of trans isomers and cis isomers in terms of the configuration of the silacyclohexane ring. If this is the case, then a conventional purification means such as chromatography and recrystallization is employed to isolate the trans isomers.

The silacyclohexane compound of this invention can be mixed with known compounds to obtain a liquid crystal composition. The compound used for mixing to obtain the liquid crystal compound can be chosen from among the known compounds shown below.

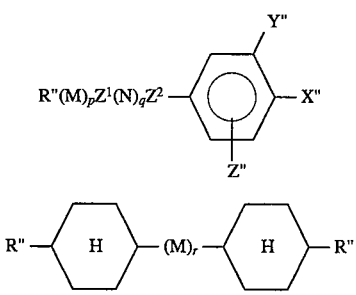

In the chemical formulas shown above, (M) and (N) denote one of the following listed in 1) through 5):

1) A trans-1,4-cyclohexylene group which has no substitution or which has one or more substitutional groups such as F, Cl, Br, CN or alkyl groups
2) A trans-1,4-cyclohexylene group in which O or S is substituted for one or nonadjacent two $CH_2$ groups in the cyclohexane ring
3) A 1,4-cyclohexenylene group
4) A 1,4-phenylene group which has no substitution or which has one or two substitutional groups such as F, Cl, $CH_3$ or CN groups
5) A 1,4-phenylene group in which an N atom is substituted for one or two CH groups in the ring $Z^1$ and $Z^2$ denote $-CH_2CH_2-$, $-CH=CH-$, $-C\equiv C-$, $-CO_2-$, $-OCO-$, $-CH_2O-$, $-OCH_2-$ or a single bond. p,q=0, 1 or 2 (where p+q=1, 2 or 3), and r=0, 1 or 2. R" denotes a linear-chain alkyl group with a carbon number of 1–10, an alkoxy group, a branched-chain alkyl group with a carbon number of 3–8, an alkoxyalkyl group with a carbon number of 2–7, or an alkenyl group with a carbon number of 2–8. X" denotes H, CN, F, Cl, $CF_3$, $CF_2Cl$, $CHFCl$, $OCF_3$, $OCF_2Cl$, $OCHFCl$, $OCHF_2$, a linear-chain alkyl or alkoxy group with a carbon number of 1–10, or an alkoxyalkyl group with a carbon number of 2–7. Y" and Z" denote H, F, Cl or $CH_3$. i and j denote 0, 1 or 2.

If p=2 and r=2, then (M) can contain heterogeneous rings, and if q=2, then (N) can contain heterogeneous rings.

The ratio of one or more types of the silacyclohexane compounds of this invention contained in the liquid crystal composition is 1–50 wt %, more preferably 5–30 wt %. The liquid crystal phase can also contain a polygenetic dye(s) to generate a colored guest-host system and additives to change the dielectric anisotropy, viscosity and the orientation of the nematic phase.

The liquid crystal phase thus formed is sealed between transparent base plates which have electrodes of desired shapes and is thus used as liquid crystal display elements. This element can have various undercoatings, overcoatings for orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method, the super twisted nematic (STN) method, the polymer dispersion (PD) method and the guest-host (GH) method can be adopted.

As described thus far, this invention provides a conventionally unknown and completely new liquid crystal compound with a high $T_{NI}$ containing silacyclohexane rings with a silicon atom(s) in its molecular structure.

The liquid crystal compounds of this invention, depending on the selection of substitutional groups, can be widely used as the base material which comprises the major component of the liquid crystal phase, in a manner similar to how the conventional liquid crystal compounds with a CECP structure of similar hydrocarbon rings are used. The liquid crystal compound whose substitutional group Z in the general formula (I) is R or OR has near-zero dielectric anisotropy, and therefore it should preferably be used for the liquid crystal phase for display based on dynamic scattering (DS) or deformation of aligned phase (PAP mode). The compounds in which Z is other than R or OR should preferably be used for manufacturing the liquid crystal phase with a large positive dielectric anisotropy which is used in display elements based on the twisted nematic cell or the cholesteric-nematic phase transition.

EXAMPLE

The details of this invention are described below by referring to specific examples.

[Example 1]

Preparation of trans, trans-4-(4-(4-n-propyl-4-silacyclohexyl)cyclohexyl)-3',4'-difluorobiphenyl A 5 ml tetrahydrofuran (hereafter referred to as "THF") solution of 2.5M n-propyl magnesium chloride (12.5 mmol) was dripped into a mixed solution of 4.1 g (10.0 mmol) of 4-(trans-4-(4-chloro-4-silacyclohexyl)cyclohexyl)-3',4'-difluorobiphenyl and 30 ml of THF. The silacyclohexane rings of the product thus obtained were a mixture of trans isomers and cis isomers. After a conventional after treatment, they were separated by means of chromatography to obtain 3.30 g (yield 80%) of the target product, i.e. the trans, trans isomers.

IR (KBr disc) vmax: 2916 (s), 2104 (s), 1533 (m), 1506 (s), 1279 (m), 985 (s), 889 (m), 844 (m) and 814 (s) cm$^{-1}$ C—S transition point: 82.7° C. N—I transition point: 229.1° C. S—N transition point: 107.5° C.

[Example 2]

The following compound was obtained in the same manner as Example 1.

Trans, trans-3-fluoro-4-(4-(4-n-propyl-4-silacyclohexyl)cyclohexyl)-4'-trifluoromethoxybiphenyl

[Example 3]

The following compound was obtained in the same manner as Example 1.

Trans, trans-4-(4-(4-n-propyl-4-silacyclohexyl)cyclohexyl)-2'-fluoro-4'-n-pentylbiphenyl

[Example 4]

Preparation of trans, trans-4-(4-(4-n-propylcyclohexyl)-4-silacyclohexyl)4'-fluorobiphenyl A 12 ml THF solution of 2.0M n-propylcyclohexyl magnesium bromide (24 mmol) was dripped into a mixed solution of 3.00 g (10.0 mmol) of 4-(4-methoxy-4-silacyclohexyl)-4'-fluorobiphenyl and 30 ml of THF. The silacyclohexane rings of the product thus obtained were a mixture of trans isomers and cis isomers. After a conventional after treatment, they were separated by means of chromatography to obtain 2.57 g (yield 65%) of the target product, i.e. trans, trans isomers.

[Example 5]

The following compound was obtained in the same manner as Example 4.

Trans, trans-4-(4-(4-n-pentylcyclohexyl)-4-silacyclohexyl)-3',4'-difluorobiphenyl

[Example 6]

The following compound was obtained in the same manner as Example 4.

Trans, trans-4-(4-fluoro-4-(4-n-pentylcyclohexyl)-4-silacyclohexyl)-3',4'-difluorobiphenyl

[Example 7]

Preparation of trans, trans-4-(4-(4-n-propyl-4-silacyclohexyl)cyclohexyl)-3',4'-difluorobiphenyl A 25 ml THF solution of 1.0M 4-(4-(3,4-difluorophenyl)phenyl)cyclohexyl magnesium bromide (25 mmol) was dripped into a mixed solution of 5.36 g (20.0 mmol) of 4-iodo-1-n-propyl-1-silacyclohexane, 50 mg of copper (I) iodide, 100 mg of triethyl phosphite and 50 ml of THF. The silacyclohexane rings of the product thus obtained were a mixture of trans isomers and cis isomers. After a conventional after treatment, they were separated by means of chromatography to obtain 1.49 g (yield 36%) of the target product, i.e. the trans, trans isomers. The obtained target product exhibited the same physical properties as the product of Example 1.

[Example 8]

Preparation of trans, trans-4-(4-(4-n-propyl-4-silacyclohexyl)cyclohexyl)-4'-fluorobiphenyl A 100 ml THF-toluene (1:1) solution of 1.0M 4-(trans-4-n-propyl-4-silacyclohexyl)cyclohexyl zinc chloride (100 mmol) was dripped into a mixed solution of 39.5 g (100 mmol) of 4-bromo-4'-fluorobiphenyl, 200 mg of tetrakis (triphenylphosphine) palladium (0) and 200 ml of THF. The silacyclohexane rings of the product thus obtained were a mixture of trans isomers and cis isomers. After a conventional after treatment, they were separated by means of chromatography to obtain 28.8 g (yield 73%) of the target product, i.e. the trans, trans isomers.

IR (KBr disc) vmax: 2920 (s), 2098 (s), 1493 (s), 1236 (s), 984 (s), 847 (s), 844 (s) and 818 (s) cm$^{-1}$ C—S transition point: 149.1° C. N—I transition point: 249.8° C. S—N transition point: 175.8° C.

[Example 9]

The following compound was obtained in the same manner as Example 8.

Trans, trans-2,6,4'-trifluoro-4-(4-(4-n-pentyl-4-silacyclohexyl)cyclohexyl)biphenyl

[Example 10]

Preparation of trans, trans-4-(4-(4-n-propyl-4-silacyclohexyl)cyclohexyl)-4'-fluorobiphenyl A 15 ml THF solution of 1.5M 4-(4-fluorophenyl)phenyl magnesium bromide (22.5 mmol) was dripped into a mixed solution of 7.0 g (20.0 mmol) of trans-4-(4-iodocyclohexyl)-1-n-propyl-1-silacyclohexane, 70 mg of copper (I) iodide and 50 ml of THF. The silacyclohexane rings of the product thus obtained were a mixture of trans isomers and cis isomers. After a conventional after treatment, they were separated by means of chromatography to obtain 2.29 g (yield 58%) of the target product, i.e. the trans, trans isomers. The obtained target product exhibited the same physical properties as the product of Example 8.

[Example 11]

The following compound was obtained in the same manner as Example 10.

Trans, trans-2-fluoro-4-(4-(4-n-pentyl-4-silacyclohexyl)cyclohexyl)-4'-n-propylbiphenyl

[Example 12]

The following compound was obtained in the same manner as Example 10.

Trans, trans-4-(4-(4-methyl-4-n-pentyl-4-silacyclohexyl)cyclohexyl)-4'-fluorobiphenyl

[Example 13]

The following compound was obtained in the same manner as Example 10.

Trans, trans-4-(4-(4-n-propyl-4-silacyclohexyl)cyclohexyl)-4'-chlorobiphenyl

[Example 14]

The following compound was obtained in the same manner as Example 10.

Trans, trans-4-(4-(4-n-propyl-4-silacyclohexyl)cyclohexyl)-4'-trifluoromethylbiphenyl

[Example 15]

The following compound was obtained in the same manner as Example 10.

Trans, trans-4-(4-(4-n-propyl-4-silacyclohexyl)cyclohexyl)-4'-n-pentyloxybiphenyl

[Example 16]

The following compound was obtained in the same manner as Example 10.

Trans, trans-4-(4-(4-n-propyl-4-silacyclohexyl)cyclohexyl)-3'-fluoro-4'-trifluoromethoxybiphenyl

[Example 17]

Preparation of trans, trans-4-(4-(4-n-pentyl-4-silacyclohexyl)cyclohexyl)-3',4'-difluorobiphenyl A 100 ml THF solution of 1.0M trans, trans-4-(4-(4-n-pentyl-4-silacyclohexyl)cyclohexyl)phenyl magnesium chloride (100 mmol) was dripped into a mixed solution of 19.3 g (100 mmol) of 3,4-difluoro-1-bromobenzene, 100 mg of 1,3-bis(diphenylphosphino)propane nickel (II) chloride and 300 ml of THF. After a conventional after treatment, the product thus obtained was purified by means of chromatography to obtain 37.8 g (yield 86%) of the target product, i.e. the trans, trans isomers.

IR (KBr disc) νmax: 2918 (s), 2106 (s), 1531 (s), 1311 (s), 985 (s), 887 (s), 835 (s) and 810 (s) cm$^{-1}$ C—S transition point: 61.2° C. N—I transition point: 227.8° C. S—N transition point: 80.3° C.

[Example 18]

The following compound was obtained in the same manner as Example 17.

Trans, trans-4-(4-(4-isopentylcyclohexyl)-4-silacyclohexyl)-4'-cyanobiphenyl

[Example 19]

The following compound was obtained in the same manner as Example 17.

Trans, trans-4-(4-(4-n-propylcyclohexyl)-4-silacyclohexyl)-3'-fluoro-4'-cyanobiphenyl

[Example 20]

The following compound was obtained in the same manner as Example 17.

Trans, trans-4-(4-(4-n-propylcyclohexyl)-4-silacyclohexyl)-4'-chloro-3'-fluorobiphenyl

[Example 21]

The following compound was obtained in the same manner as Example 17.

Trans, trans-4-(4-(4-n-propylcyclohexyl)-4-silacyclohexyl)-3',4',5'-trifluorobiphenyl IR (KBr disc) νmax: 2922, 2850, 2085, 1614, 1535, 1508, 1047, 985, 889 and 816 cm$^{-1}$ C—S transition point: 78.3° C. N—I transition point: 215.2° C. S—N transition point: 80.3° C.

[Example 22]

Preparation of trans, trans-4-(4-(4-n-pentyl-4-silacyclohexyl)silacyclohexyl)-4'-fluorobiphenyl A 25 ml THF solution of 2.2M p-fluorophenyl zinc chloride (55 mmol) was dripped into a mixed solution of 19.1 g (40 mmol) of trans, trans-4-(4-(4-n-pentyl-4-silacyclohexyl) silacyclohexyl) phenyltrifluoromethane sulfonate, 200 mg of tetrakis (triphenylphosphine) palladium (0), 3.5 g of lithium chloride and 200 ml of 1,4-dioxane. After a conventional after treatment, the product thus obtained was purified by means of chromatography to obtain 14.4 g (yield 85%) of the target product, i.e. the trans, trans isomers.

IR (KBr disc) νmax: 2918 (s), 2098 (m), 1493 (s), 1448 (m), 1236 (s), 985 (m), 846 (s) and 818 (s) cm$^{-1}$ C—S transition point: 117.3° C. N—I transition point: 243.7° C. S—N transition point: 154.8° C.

[Example 23]

The following compound was obtained in the same manner as Example 22.

Trans, trans-4-(4-(4-n-propyl-4-silacyclohexyl)silacyclohexyl)-4'-fluorobiphenyl

[Example 24]

The following compound was obtained in the same manner as Example 22.

Trans, trans-2,6-difluoro-4-(4-(4-n-pentyl-4-silacyclohexyl)cyclohexyl)-4'-trifluoromethoxybiphenyl

[Example 25]

The following compound was obtained in the same manner as Example 22.

Trans, trans-4-(4-(4-n-pentyl-4-silacyclohexyl)cyclohexyl)-4'-(3-methoxypropyl)biphenyl

[Example 26]

The following compound was obtained in the same manner as Example 22.

Trans, trans-4-(4-(4-n-pentyl-4-silacyclohexyl)cyclohexyl)-4'-difluoromethoxybiphenyl

[Example 27]

The following compound was obtained in the same manner as Example 22.

Trans, trans-4-(4-(4-n-pentyl-4-silacyclohexyl)cyclohexyl)-3',5'-difluoro-4'-difluoromethoxybiphenyl

[Example 28]

The following compound was obtained in the same manner as Example 22.

Trans, trans-4-(4-(4-n-pentyl-4-silacyclohexyl)cyclohexyl)-4'-chloro-3',5'-difluorobiphenyl

[Example 29]

The following compound was obtained in the same manner as Example 22.

Trans, trans-4-(4-(4-(3-methoxypentyl)-4-silacyclohexyl)cyclohexyl)-4'-fluorobiphenyl

[Example 30]

The following compound was obtained in the same manner as Example 22.

Trans, trans-4-(4-(4-(1-propenyl)-4-silacyclohexyl)cyclohexyl)-3',4'-difluorobiphenyl

[Example 31]

The following compound was obtained in the same manner as Example 22.

Trans, trans-4-(4-(4-n-pentyloxycyclohexyl)-4-silacyclohexyl)-3',4'-difluorobiphenyl

[Example 32]

The following compound was obtained in the same manner as Example 22.

Trans, trans-2-fluoro-4-(4-(4-n-pentyl-4-silacyclohexyl)cyclohexyl)-4'-fluorobiphenyl IR (KBr disc) νmax: 2918, 22850, 2090, 1491, 1225, 985, 939, 883, 825 and 818 cm$^{-1}$ C—N transition point: 75.5° C. N—I transition point: 230.6° C.

[Example 33]

The following compound was obtained in the same manner as Example 22.

Trans, trans-2-fluoro-4-(4-(4-n-pentyl-4-silacyclohexyl)cyclohexyl)-4'-trifluoromethoxybiphenyl IR (KBr disc) νmax: 2922, 2850, 2104, 1493, 1275, 1219, 1161, 885 and 816 cm$^{-1}$ C—S transition point: 46.5° C. S—N transition point: 145.5° C. N—I transition point: 235.7° C.

[Example 34]

The following compound was obtained in the same manner as Example 22.

Trans, trans-4-(4-(4-fluorobutyl)-4-silacyclohexyl)cyclohexyl)-3',4'-difluorobiphenyl

[Example 35]

Preparation of trans, trans-4-(2-(4-n-propyl-4-silacyclohexyl)cyclohexyl)ethyl)-3',4'-difluorobiphenyl 2.5 g (20 mmol) of n-propyl bromide was dripped into a mixture of 0.5 g (21 mmol) of magnesium and 50 ml of THF to obtain a Grignard's reagent. This solution was then dripped into a 50 ml THF solution of 8.7 g (20 mmol) of 4-(2-(trans-4-(4-chloro-4-silacyclohexyl)cyclohexyl)ethyl)-3',4'-difluorobiphenyl to obtain a crude product. The silacyclohexane rings of this product were a mixture of trans isomers and cis isomers. After a conventional after treatment, they were separated by means of chromatography to obtain 7.8 g (yield 88%) of the target product, i.e. the trans, trans isomers. C—S transition point: 59.8° C. S—N transition point: 71.7° C. N—I transition point: 199.4° C.

IR (KBr disc) νmax: 2916, 2850, 2104, 1506, 1279, 981, 889, 843, 810 and 777 cm$^{-1}$ The following silacyclohexane compounds were obtained in the same manner as Example 35.

[Example 36]

Trans, trans-4-(2-(4-(4-n-propyl-4-silacyclohexyl)cyclohexyl)ethyl)-3-fluoro-4'-trifluoromethoxybiphenyl

[Example 37]
Trans, trans-4-(2-(4-(4-n-propyl-4-silacyclohexyl)cyclohexyl)ethyl)-2'-fluoro-4"-pentylbiphenyl
[Example 38]
Preparation of trans, trans-4-(2-(4-n-propylcyclohexyl)-4-silacyclohexyl)ethyl)-4'-fluorobiphenyl 4.1 g (20 mmol) of trans-4-n-propylcyclohexyl bromide was dripped into a mixture of 0.5 g (21 mmol) of magnesium and 50 ml of THF to obtain a Grignard's reagent. This solution was then dripped into a 50 ml THF solution of 6.6 g (20 mmol) of 4-(2-(4-methoxy-4-silacyclohexyl)ethyl)-4'-fluorobiphenyl to obtain a crude product. The silacyclohexane rings of this product were a mixture of trans isomers and cis isomers. After a conventional after treatment, they were separated by means of chromatography to obtain 7.3 g (yield 86%) of the target product, i.e. the trans, trans isomers.

The following compounds were obtained in the same manner as Example 38.
[Example 39]
Trans, trans-4-(2-(4-(4-n-pentylcyclohexyl)-4-silacyclohexyl)ethyl)-3',4'-difluorobiphenyl
[Example 40]
Trans, trans-4-(2-(4-(4-n-pentylcyclohexyl)-4-fluoro-silacyclohexyl)ethyl)-3',4'-difluorobiphenyl
[Example 41]
Preparation of trans, trans-4-(2-(4-(4-n-propyl-4-silacyclohexyl)cyclohexyl)ethyl)-3',4'-difluorobiphenyl 7.6 g (20 mmol) of 4-(2-(4-bromocyclohexyl)ethyl)-3',4'-difluorobiphenyl was dripped into a mixture of 0.5 g (21 mmol) of magnesium and 50 ml of THF to obtain a Grignard's reagent. This solution was then dripped into a 50 ml THF solution of 5.4 g (20 mmol) of 4-iodo-1-n-propyl-1-silacyclohexane and a catalytic amount of cuprous chloride to obtain a crude product. The silacyclohexane rings of this product were a mixture of trans isomers and cis isomers. After a conventional after treatment, they were separated by means of chromatography to obtain 3.8 g (yield 43%) of the target product, i.e. the trans, trans isomers. The obtained target product exhibited the same physical properties as the product of Example 1.
[Example 42]
Preparation of trans, trans-4-(2-(4-(4-n-propyl-4-silacyclohexyl)cyclohexyl)ethyl)-4'-fluorobiphenyl 6.3 g (20 mmol) of 4-(4-bromomethylcyclohexyl)-1-n-propyl-1-silacyclohexane was dripped into a mixture of 0.5 g (21 mmol) of magnesium and 50 ml of THF to obtain a Grignard's reagent. This solution was then dripped into a 50 ml THF solution of 5.3 g (20 mmol) of 4'-bromomethyl-4'-fluorobiphenyl and catalytic amounts of copper (I) iodide and triethyl phosphite to obtain a crude product. The silacyclohexane rings of this product were a mixture of trans isomers and cis isomers. After a conventional after treatment, they were separated by means of chromatography to obtain 7.7 g (yield 91%) of the target product, i.e. the trans, trans isomers. C—S transition point: 89.5° C. S—N transition point: 148.8° C. N—I transition point: 224.7° C.

IR (KBr disc) vmax: 2918, 2852, 2102, 1498, 1225, 1161, 889, 843 and 820 cm$^{-1}$ The following silacyclohexane compounds were obtained in the same manner as Example 42.
[Example 43]
Trans, trans-4-(2-(4-(4-n-pentyl-4-silacyclohexyl)cyclohexyl)ethyl)-2,6,4'-trifluorobiphenyl
[Example 44]
Trans, trans-4-(2-(4-(4-n-pentyl-4-silacyclohexyl)cyclohexyl)ethyl)-2-fluoro-4'-n-pentylbiphenyl
[Example 45]
Preparation of trans, trans-4-(2-(4-(4-n-propyl-4-silacyclohexyl)cyclohexyl)ethyl)-4'-fluorobiphenyl 6.6 g (20 mmol) of 4-(4-(2-bromoethyl)cyclohexyl)-1-n-propyl-1-silacyclohexane was dripped into a mixture of 0.5 g (21 mmol) of magnesium and 50 ml of THF to obtain a Grignard's reagent. This solution was then dripped into a 50 ml THF solution of 5.0 g (20 mmol) of 4-bromo-4'-fluorobiphenyl and a catalytic amount of tetrakis (triphenylphosphine) palladium (0) to obtain a crude product. The silacyclohexane rings of this product were a mixture of trans isomers and cis isomers. After a conventional after treatment, they were separated by means of chromatography to obtain 7.6 g (yield 90%) of the target product, i.e. the trans, trans isomers. The obtained target product exhibited the same physical properties as the product of Example 8.

The following silacyclohexane compounds were obtained in the same manner as Example 45.
[Example 46]
Trans, trans-4-(2-(4-(4-n-pentyl-4-methyl-4-silacyclohexyl)cyclohexyl)ethyl)-4'-fluorobiphenyl
[Example 47]
Trans, trans-4-(2-(4-(4-n-propyl-4-silacyclohexyl)cyclohexyl)ethyl)-4'-trifluoromethylbiphenyl
[Example 48]
Preparation of trans, trans-4-(2-(4-(4-n-propyl-4-silacyclohexyl)cyclohexyl)ethyl)-4'-chloro-3'-fluorobiphenyl 6.0 g (20 mmol) of 4-bromomethyl-4'-chloro-3'-fluorobiphenyl was dripped into a mixture of 0.5 g (21 mmol) of magnesium and 50 ml of THF to obtain a Grignard's reagent. This solution was then dripped into a 50 ml THF solution of 6.3 g (20 mmol) of 4-(4-bromomethylcyclohexyl)-1-n-propyl-1-silacyclohexane and catalytic amounts of copper (I) iodide and triethyl phosphite to obtain a crude product. The silacyclohexane rings of this product were a mixture of trans isomers and cis isomers. After a conventional after treatment, they were separated by means of chromatography to obtain 7.5 g (yield 82%) of the target product, i.e. the trans, trans isomers. C—N transition point: 63.3° C. N—I transition point: 208.0° C.

IR (KBr disc) vmax: 2920, 2850, 2096, 1481, 1200, 1070, 982, 889, 845, 804 and 741 cm$^{-1}$ The following silacyclohexane compounds were obtained in the same manner as Example 48.
[Example 49]
Trans, trans-4-(2-(4'-(4-n-propyl-4-silacyclohexyl)cyclohexyl)ethyl)-4'-n-pentyloxybiphenyl
[Example 50]
Trans, trans-4-(2-(4-(4-n-propyl-4-silacyclohexyl)cyclohexyl)ethyl)-3'-fluoro-4'-trifluoromethoxybiphenyl
[Example 51]
Trans, trans-4-(2-(4-(4-isopentylcyclohexyl)-4-silacyclohexyl)ethyl)-4'-cyanobiphenyl
[Example 52]
Preparation of trans, trans-4-(2-(4-(4-n-pentyl-4-silacyclohexyl)cyclohexyl)ethyl)-3',4'-difluorobiphenyl 8.7 g (20 mmol) of 4-(2-(4-n-pentyl-4-silacyclohexyl)cyclohexyl)ethyl)-1-bromobenzene was dripped into a mixture of 0.5 g (21 mmol) of magnesium and 50 ml of THF to obtain a Grignard's reagent. This was dripped into a 20 ml THF solution of 2.8 g (20 mmol) of zinc chloride to obtain an organozinc reagent. This solution was then dripped into a 50 ml THF solution of 3.9 g (20 mmol) of 3,4-difluorobenzene and a catalytic amount of tetrakis (triphenylphosphine) palladium (0) to obtain a crude product. The silacyclohexane rings of this product were a mixture of trans isomers and cis isomers. After a conventional after treatment, they were separated by means of chromatography to obtain 3.9 g (yield 42%) of the target product, i.e. the trans, trans isomers. C—N transition point: 129.2° C. N—I transition point: 231.1° C.

IR (KBr disc) νmax: 2918, 2848, 2100, 1487, 1095, 981, 887, 842, 810 and 746 cm$^{-1}$ The following silacyclohexane compound was obtained in the same manner as Example 52.

[Example 53]
Trans, trans-4-(2-(4-(4-n-propyl-4-silacyclohexyl)cyclohexyl)ethyl)-3'-fluoro-4'-cyanobiphenyl

[Example 54]
Preparation of trans, trans-4-(2-(4-(4-n-propyl-4-silacyclohexyl)cyclohexyl)ethyl)-4'-chlorobiphenyl 8.8 g (20 mmol) of 4-chlorobromobenzene was dripped into a mixture of 0.5 g (21 mmol) of magnesium and 50 ml of THF to obtain a Grignard's reagent. This was dripped into a 20 ml THF solution of 2.8 g (20 mmol) of zinc chloride to obtain an organozinc reagent. This solution was then dripped into a 50 ml THF solution of 8.2 g (20 mmol) of 4-(2-(4-n-propyl-4-silacyclohexyl)cyclohexyl)ethyl)-1-bromobenzene and a catalytic amount of 1,3-bis(diphenylphosphino)propane nickel (II) chloride to obtain a crude product. The silacyclohexane rings of this product were a mixture of trans isomers and cis isomers. After a conventional after treatment, they were separated by means of chromatography to obtain 7.2 g (yield 82%) of the target product, i.e. the trans, trans isomers.

The following silacyclohexane compounds were obtained in the same manner as Example 54.

[Example 55]
Trans, trans-4-(2-(4-(4-n-propyl-4-silacyclohexyl)cyclohexyl)ethyl)-3',4',5'-trifluorobiphenyl

[Example 56]
Trans, trans-4-(2-(4-(4-n-pentyl-4-silacyclohexyl)cyclohexyl)ethyl)-4'-fluorobiphenyl

[Example 57]
Trans, trans-4-(2-(4-(4-n-propyl-4-silacyclohexyl)-4-silacyclohexyl)ethyl)-4'-fluorobiphenyl

[Example 58]
Trans, trans-4-(2-(4-(4-n-pentyl-4-silacyclohexyl)cyclohexyl)ethyl)-2,6-difluoro-4'-trifluoromethoxybiphenyl

[Example 59]
Trans, trans-4-(2-(4-(4-n-pentyl-4-silacyclohexyl)cyclohexyl)ethyl)-4'-(3-methoxypropyl)biphenyl

[Example 60]
Trans, trans-4-(2-(4-(4-n-pentyl-4-silacyclohexyl)cyclohexyl)ethyl)-4'-difluoromethoxybiphenyl

[Example 61]
Trans, trans-4-(2-(4-(4-n-pentyl-4-silacyclohexyl)cyclohexyl)ethyl)-3',5'-difluoro-4'-difluoromethoxybiphenyl

[Example 62]
Trans, trans-4-(2-(4-(4-n-pentyl-4-silacyclohexyl)cyclohexyl)ethyl)-3',5'-difluoro-4'-chlorobiphenyl

[Example 63]
Trans, trans-4-(2-(4-(4-(3-methoxypropyl)-4-silacyclohexyl)cyclohexyl)ethyl)-4'-fluorobiphenyl

[Example 64]
Trans, trans-4-(2-(4-(4-(1-propenyl)-4-silacyclohexyl)cyclohexyl)ethyl)-3',4'-difluorobiphenyl

[Example 65]
Trans, trans-4-(2-(4-(-4-n-pentyloxycyclohexyl)-4-silacyclohexyl)ethyl)-3',4'-difluorobiphenyl

[Example 66]
Trans, trans-4-(2-(4-(4-n-pentyl-4-silacyclohexyl)cyclohexyl)ethyl)-2',3'-diffuoro-4'-ethoxybiphenyl

[Example 67]
Preparation of 4-(trans-4-(2-(trans-4-n-propyl-4-silacyclohexyl)ethyl)cyclohexyl)-4''-cyanobiphenyl 12.5 g (0.1 mol) of n-propyl bromide was dripped into a mixture of 2.5 g (0.1 mol) of magnesium and 500 ml of THF to obtain a Grignard's reagent. This solution was then dripped into a 300 ml THF solution of 42 g (0.1 mol) of 4-(trans-4-(2-(4-chloro-4-silacyclohexyl)ethyl)cyclohexyl)-4'-cyanobiphenyl to obtain 4-(trans-4-(2-(trans-4-n-propyl-4-silacyclohexyl)ethyl)cyclohexyl)-4'-cyanobiphenyl. The silacyclohexane rings of the product were a mixture of trans isomers and cis isomers. They were separated by means of chromatography to obtain 32.8 g (yield 76.4%) of the trans isomer.

[Example 68]
Preparation of 4-(trans-4-(2-(trans-4-n-pentyl-4-silacyclohexyl)ethyl)cyclohexyl)-3'-fluoro-4'-chlorobiphenyl 10.7 g (0.1 mol) of n-pentyl chloride was dripped into a mixture of 2.5 g (0.1 mol) of magnesium and 300 ml of THF to obtain a Grignard's reagent. This solution was then dripped into a 300 ml THF solution of 45 g (0.1 mol) of 4-(trans-4-(2-(4-chloro-4-silacyclohexyl)ethyl)cyclohexyl)-3'-fluoro-4'-chlorobiphenyl to obtain 4-(trans-4-(2-(trans-4-n-pentyl-4-silacyclohexyl)ethyl)cyclohexyl)-3'-fluoro-4'-chlorobiphenyl. The silacyclohexane rings of the product were a mixture of trans isomers and cis isomers. They were separated by means of chromatography to obtain 31.3 g (yield 69.9%) of the trans isomer.

[Example 69]
Preparation of 4-(trans-4-(2-(trans-4-n-pentyl-4-silacyclohexyl)ethyl)cyclohexyl)-2-fluoro-4'-trifluoromethoxybiphenyl 4-(trans-4-(2-(trans-4-n-pentyl-4-silacyclohexyl)ethyl)cyclohexyl-2-fluoro-4'-trifluoromethoxybiphenyl was obtained by the same method as Example 68 except for the fact that 4-(trans-4-(2-(4-chloro-4-silacyclohexyl)ethyl)cyclohexyl)-2-fluoro-4'-trifluoromethoxybiphenyl was used instead of the 4-(trans-4-(2-(4-chloro-4-silacyclohexyl)ethyl)cyclohexyl)-3'-fluoro-4'-chlorobiphenyl in Example 68. The silacyclohexane rings of the product were a mixture of trans isomers and cis isomers. They were separated by means of chromatography to obtain 44.4 g (yield 83.1%) of the trans isomer.

[Example 70]
Preparation of 4-(trans-4-(2-(trans-4-n-pentyl-4-silacyclohexyl)ethyl)cyclohexyl)-2,6-difluoro-4'-difluoromethoxybiphenyl 4-(trans-4-(2-(trans-4-n-pentyl-4-silacyclohexyl)ethyl)cyclohexyl)-2,6-difluoro-4'-difluoromethoxybiphenyl was obtained by the same method as Example 68 except for the fact that 4-(trans-4-(2-(4-chloro-4-silacyclohexyl)ethyl)cyclohexyl)-2,6-difluoro-4'-difluoromethoxybiphenyl was used instead of the 4-(trans-4-(2-(4-chloro-4-silacyclohexyl)ethyl)cyclohexyl)-3'-fluoro-4'-chlorobiphenyl in Example 68. The silacyclohexane rings of the product were a mixture of trans isomers and cis isomers. They were separated by means of chromatography to obtain 34.1 g (yield 63.7%) of the trans isomer.

[Example 71]
Preparation of 4-(trans-4-(2-(trans-4-n-butyl-cis-4-methyl-4-silacyclohexyl)ethyl)4-silacyclohexyl)-2,3',5'-trifluoro-4'-chlorobiphenyl A hexane solution of 1.6M butyl lithium was dripped into a 300 ml hexane solution of 50 g (0.1 mol) of 4-(trans-4-(2-(4-chloro-4-methyl-4-silacyclohexyl)ethyl)4-silacyclohexyl)-2,3',5'-trifluoro-4'-chlorobiphenyl to obtain 4-(trans-4-(2-(trans-4-n-butyl-cis-4-methyl-4-silacyclohexyl)ethyl)4-silacyclohexyl)-2,3',5'-trifluoro-4'-chlorobiphenyl. The silacyclohexane rings of the product were a mixture of trans isomers and cis isomers. They were separated by means of chromatography to obtain 41.6 g (yield 75.5%) of the trans isomer.

[Example 72]

Preparation of 4-(trans-4-(2-(trans-4-n-pentyl-4-silacyclohexyl)ethyl)cyclohexyl)-4'-fluorobiphenyl 24.9 g (0.1 mol) of 1-bromo-4-n-pentyl-4-silacyclohexane was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 36.1 g (0.1 mol) of 4-(trans-4-(2-bromoethyl)cyclohexyl)-4'-fluorobiphenyl. After a conventional after treatment, 4-(trans-4-(2-(trans-4-n-pentyl-4-silacyclohexyl)ethyl)cyclohexyl)-4'-fluorobiphenyl was obtained. The silacyclohexane rings of the product were a mixture of trans isomers and cis isomers. They were separated by means of chromatography to obtain 30.5 g (yield 67.6%) of the trans isomer.

[Example 73]

Preparation of 4-(trans-4-(2-(trans-4-n-propyl-4-silacyclohexyl)ethyl)cyclohexyl)-8'-fluoro-4'-trifluoromethylbiphenyl 22.1 g (0.1 mol) of 1-bromo-4-n-propyl-4-silacyclohexane was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 47.6 g (0.1 mol) of 4-(trans-4-(2-iodoethyl)cyclohexyl)-3'-fluoro-4'-trifluoromethylbiphenyl. After a conventional after treatment, 4-(trans-4-(2-(trans-4-n-propyl-4-silacyclohexyl)ethyl)cyclohexyl)-3'-fluoro-4'-trifluoromethylbiphenyl was obtained. The silacyclohexane rings of the product were a mixture of trans isomers and cis isomers. They were separated by means of chromatography to obtain 35.5 g (yield 72.3%) of the trans isomer.

[Example 74]

Preparation of 4-(trans-4-(2-(trans-4-n-propyl-4-silacyclohexyl)ethyl)cyclohexyl)-2,3'-difluoro-4'-difluoromethoxybiphenyl 22.1 g (0.1 mol) of 1-bromo-4-n-propyl-4-silacyclohexane was dripped into a mixture of 2.5 g (0.11 mol) of magnesium and 300 ml of THF to obtain a Grignard's reagent. This solution was then dripped into a 500 ml THF solution of 1 g of Li2CuCl4 and 52.1 g (0.1 mol) of 4-(trans-4-(tosyloxyethyl)cyclohexyl)-3'-fluoro-4'-trifluoromethylbiphenyl. After a conventional after treatment, 4-(trans-4-(2-(trans-4-n-propyl-4-silacyclohexyl)ethyl)cyclohexyl)-2,3'-difluoro-4'-difluoromethoxybiphenyl was obtained. The silacyclohexane rings of the product were a mixture of trans isomers and cis isomers. They were separated by means of chromatography to obtain 38.0 g (yield 75.0%) of the trans isomer.

[Example 75]

Preparation of 4-(trans-4-(2-(trans-4-n-propyl-4-silacyclohexyl)ethyl)cyclohexyl)-2,6-difluoro-4'-trifluoromethoxybiphenyl 4-(trans-4-(2-(trans-4-n-propyl-4-silacyclohexyl)ethyl)cyclohexyl)-2,6-difluoro-4'-trifluoromethoxybiphenyl was obtained by the same method as Example 74 except for the fact that 46.3 g of 4-(trans-4-(2-mesyloxyethyl)cyclohexyl)-2,6-difluoro-4'-trifluoromethoxybiphenyl was used instead of the 4-(trans-4-(2-tosyloxyethyl)cyclohexyl)-3'-fluoro-4'-trifluoromethylbiphenyl in Example 74. The silacyclohexane rings of the product were a mixture of trans isomers and cis isomers. They were separated by means of chromatography to obtain 39.2 g (yield 74.8%) of the trans isomer.

[Example 76]

Preparation of 4-(trans-4-(2-(trans-4-n-propyl-4-silacyclohexyl)ethyl)cyclohexyl)-2,3',5'-trifluoro-4'-trifluoromethoxybiphenyl 4-(trans-4-(2-(trans-4-n-propyl-4-silacyclohexyl)ethyl)cyclohexyl)-2,3',5'-trifluoro-4'-trifluoromethoxybiphenyl was obtained by the same method as Example 74 except for the fact that 54.3 g of 4-(trans-4-(2-benzenesulfonyloxyethyl)cyclohexyl)-2,3',5'-trifluoro-4'-trifluoromethoxybiphenyl was used instead of the 4-(trans-4-(2-tosyloxyethyl)cyclohexyl)-3'-fluoro-4'-trifluoromethylbiphenyl in Example 74. The silacyclohexane rings of the product were a mixture of trans isomers and cis isomers. They were separated by means of chromatography to obtain 46.2 g (yield 85.1%) of the trans isomer.

[Example 77]

Preparation of 4-(trans-4-(2-(trans-4-n-propyl-4-silacyclohexyl)ethyl)cyclohexyl)-4'-chlorobiphenyl 37.8 g (0.1 mol) of 4-(trans-4-(2-bromoethyl)cyclohexyl)-4'-chlorobiphenyl was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 22.1 g (0.1 mol) of 1-bromo-4-n-propyl-4-silacyclohexane. After a conventional after treatment, 4-(trans-4-(2-(trans-4-n-propyl-4-silacyclohexyl)ethyl)cyclohexyl)-4'-chlorobiphenyl was obtained. The silacyclohexane rings of the product were a mixture of trans isomers and cis isomers. They were separated by means of chromatography to obtain 10.0 g (yield 22.8%) of the trans isomer.

[Example 78]

Preparation of 4-(trans-4-(2-(trans-4-n-pentyl-4-silacyclohexyl)ethyl)cyclohexyl)-3'-fluoro-4'-trifluoromethoxybiphenyl 44.5 g (0.1 mol) of 4-(trans-4-(2-bromoethyl)cyclohexyl)-3'-fluoro-4'-trifluoromethoxybiphenyl was dripped into a mixture of 2.5 g (0.11 mol) of magnesium and 300 ml of THF to obtain a Grignard's reagent. This solution was then dripped into a 500 ml THF solution of 20.5 g (0.1 mol) of 1-chloro-1-n-pentyl-silacyclohexane. After a conventional after treatment, 4-(trans-4-(2-(trans-4-n-pentyl-4-silacyclohexyl)ethyl)cyclohexyl)-3'-fluoro-4'-trifluoromethoxybiphenyl was obtained. The silacyclohexane rings of the product were a mixture of trans isomers and cis isomers. They were separated by means of chromatography to obtain 44.9 g (yield 84.1%) of the trans isomer.

[Example 79]

Preparation of 4-(trans-4-(2-(trans-4-n-propyl-4-silacyclohexyl)ethyl)cyclohexyl)-2',3'-difluoro-4'-methoxybiphenyl 4-(trans-4-(2-(trans-4-n-propyl-4-silacyclohexyl)ethyl)cyclohexyl)-2',3'-difluoro-4'-methoxybiphenyl was obtained by the same method as Example 77 except for the fact that 39.3 g of 4-(trans-4-(2-bromoethyl)cyclohexyl)-2',3'-difluoro-4'-methoxybiphenyl was used instead of the 4-(trans-4-(2-bromoethyl)cyclohexyl)-4'-chlorobiphenyl in Example 77. The silacyclohexane rings of the product were a mixture of trans isomers and cis isomers. They were separated by means of chromatography to obtain 12.0 g (yield 26.3%) of the trans isomer.

[Example 80]

Preparation of 4-(trans-4-(2-(trans-4-n-propyl-4-silacyclohexyl)ethyl)cyclohexyl)-3',5'-difluoro-4'-chlorobiphenyl 4-(trans-4-(2-(trans-4-n-propyl-4-silacyclohexyl)ethyl)cyclohexyl)-3',5'-difluoro-4'-chlorobiphenyl was obtained by the same method as Example 77 except for the fact that 41.4 g of 4-(trans-4-(2-bromoethyl)cyclohexyl)-3',5'-difluoro-4'-chlorobiphenyl was used instead of the 4-(trans-4-(2-bromoethyl)cyclohexyl)-4'-chlorobiphenyl in Example 77. The silacyclohexane rings of the product were a mixture of trans isomers and cis isomers. They were separated by means of chromatography to obtain 13.3 g (yield 28.1%) of the trans isomer.

[Example 81]
Preparation of 4-(trans-4-(2-(trans-4-n-propyl-4-silacyclohexyl)ethyl)cyclohexyl)-2,6,3',4',5'-pentafluorobiphenyl 4-(trans-4-(2-(trans-4-n-propyl-4-silacyclohexyl)ethyl)cyclohexyl)-2,6,3',4',5'-pentafluorobiphenyl was obtained by the same method as Example 77 except for the fact that 35.3 g of 4-(trans-4-(2-bromoethyl)cyclohexyl)-2,6,3',4',5'-pentafluorobiphenyl was used instead of the 4-(trans-4-(2-bromoethyl)cyclohexyl)-4'-chlorobiphenyl in Example 77. The silacyclohexane rings of the product were a mixture of trans isomers and cis isomers. They were separated by means of chromatography to obtain 11.3 g (yield 22.9%) of the trans isomer.

[Example 82]
Preparation of 4-(trans-4-(2-(trans-4-n-pentyl-4-silacyclohexyl)ethyl)cyclohexyl)-4'-trifluoromethylbiphenyl 26.3 g (0.1 mol) of trans-1-bromomethyl-4-n-pentyl-4-silacyclohexane was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 44.4 g (0.1 mol) of 4-(trans-4-iodomethylcyclohexyl)-4'-trifluoromethylbiphenyl. After a conventional after treatment, purification was conducted by means of chromatography to obtain 38.5 g (yield 76.9%) of 4-(trans-4-(2-(trans-4-n-pentyl-4-silacyclohexyl)ethyl)cyclohexyl)-4'-trifluoromethylbiphenyl was obtained.

[Example 83]
Preparation of 4-(trans-4-(2-(trans-4-n-pentyl-4-silacyclohexyl)ethyl)cyclohexyl)-3'-fluoro-4'-difluoromethoxybiphenyl 35.0 g (yield 67.7%) of 4-(trans-4-(2-(trans-4-n-pentyl-4-silacyclohexyl)ethyl)cyclohexyl)-3'-fluoro-4'-difluoromethoxybiphenyl was obtained by the same method as Example 82 except for the fact that 41.3 g of 4-(trans-4-bromomethylcyclohexyl)-3'-fluoro-4'-difluoromethoxybiphenyl was used instead of the 4-(trans-4-iodomethylcyclohexyl)-4'-trifluoromethylbiphenyl in Example 82.

[Example 84]
Preparation of 4-(trans-4-(2-(trans-4-n-pentyl-4-silacyclohexyl)ethyl)cyclohexyl)-2,3'-difluoro-4'-difluoromethoxybiphenyl 42.9 g (yield 80.3%) of 4-(trans-4-(2-(trans-4-n-pentyl-4-silacyclohexyl)ethyl)cyclohexyl)-2,3'-difluoro-4'-difluoromethoxybiphenyl was obtained by the same method as Example 82 except for the fact that 50.7 g of 4-(trans-4-tosyloxymethylcyclohexyl)-2,3'-difluoro-4'-difluoromethoxybiphenyl was used instead of the 4-(trans-4-iodomethylcyclohexyl)-4'-trifluoromethylbiphenyl in Example 82.

[Example 85]
Preparation of 4-(trans-4-(2-(trans-4-n-pentyl-4-silacyclohexyl)ethyl)cyclohexyl)-2,6-difluoro-4'-trifluoromethylbiphenyl 39.3 g (yield 73.2%) of 4-(trans-1-(2-(trans-4-n-pentyl-4-silacyclohexyl)ethyl)cyclohexyl)-2,6-difluoro-4'-trifluoromethylbiphenyl was obtained by the same method as Example 82 except for the fact that 43.3 g of 4-(trans-4-mesyloxymethylcyclohexyl)-2,6-difluoro-4'-trifluoromethylbiphenyl was used instead of the 4-(trans-4-iodomethylcyclohexyl)-4'-trifluoromethylbiphenyl in Example 82.

[Example 86]
Preparation of 4-(trans-4-(2-(trans-4-n-pentyl-4-silacyclohexyl)ethyl)cyclohexyl)-2,3',5'-trifluoro-4'-difluoromethoxybiphenyl 41.0 g (yield 74.2%) of 4-(trans-4-(2-(trans-4-n-pentyl-4-silacyclohexyl)ethyl)cyclohexyl)-2,3',5'-trifluoro-4'-difluoromethoxybiphenyl was obtained by the same method as Example 82 except for the fact that 41.6 g of 4-(trans-4-benzenesulfonyloxymethylcyclohexyl)-2,3',5'-trifluoro-4'-difluoromethoxybiphenyl was used instead of the 4-(trans-4-iodomethylcyclohexyl)-4'-trifluoromethylbiphenyl in Example 82.

[Example 87]
Preparation of 4-(trans-4-(2-(trans-4-n-propyl-4-silacyclohexyl)ethyl)cyclohexyl)-4'-trifluoromethoxybiphenyl 39.7 g (0.1 mol) of 4-(trans-4-bromomethylcyclohexyl)-4'-trifluoromethoxybiphenyl was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 23.5 g (0.1 mol) of trans-1-bromomethyl-4-n-propyl-4-silacyclohexane. After a conventional after treatment, purification was conducted by means of chromatography to obtain 43.0 g (yield 88.0%) of 4-(trans-4-(2-(trans-4-n-propyl-4-silacyclohexyl)ethyl)cyclohexyl)-4'-trifluoromethoxybiphenyl was obtained.

[Example 88]
Preparation of 4-(trans-4-(2-(trans-4-(4-pentenyl)-4-silacyclohexyl)ethyl)cyclohexyl)-3'-fluoro-4'-ethoxybiphenyl 39.1 g (0.1 mol) of 4-(trans-4-bromomethylcyclohexyl)-3'-fluoro-4'-ethoxybiphenyl was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 26.1 g (0.1 mol) of trans-1-bromomethyl-4-(4-pentenyl)-4-silacyclohexane. After a conventional after treatment, purification was conducted by means of chromatography to obtain 35.1 g (yield 71.3%) of 4-(trans-4-(2-(trans-4-(4-pentenyl)-4-silacyclohexyl)ethyl)cyclohexyl)-3'-fluoro-4'-ethoxybiphenyl.

[Example 89]
Preparation of 4-(trans-4-(2-(trans-4-n-propyl-4-silacyclohexyl)ethyl)cyclohexyl)-2,3-difluoro-4'-methoxybiphenyl 34.2 g (yield 72.7%) of 4-(trans-4-(2-(trans-4-n-propyl-4-silacyclohexyl)ethyl)cyclohexyl)-2,3-difluoro-4'-methoxybiphenyl was obtained by the same method as Example 87 except for the fact that 39.5 g of 4-(trans-4-bromomethylcyclohexyl)-2,3-difluoro-4'-methoxybiphenyl was used instead of the 4-(trans-4-bromomethylcyclohexyl)-4'-trifluoromethoxybiphenyl in Example 87.

[Example 90]
Preparation of 4-(trans-4-(2-(trans-4-n-propyl-4-silacyclohexyl)ethyl)cyclohexyl)-2,6,3',4'-tetrafluorobiphenyl 27.3 g (yield 57.2%) of 4-(trans-4-(2-(trans-4-n-propyl-4-silacyclohexyl)ethyl)cyclohexyl)-2,6,3',4'-tetrafluorobiphenyl was obtained by the same method as Example 87 except for the fact that 40.1 g of 4-(trans-4-bromomethylcyclohexyl)-2,6,3',4'-tetrafluorobiphenyl was used instead of the 4-(trans-4-bromomethylcyclohexyl)-4'-trifluoromethoxybiphenyl in Example 87.

[Example 91]
Preparation of 4-(trans-4-(2-(trans-4-n-propyl-4-silacyclohexyl)ethyl)cyclohexyl)-2,4'-difluorobiphenyl 38.3 g (0.1 mol) of 4-(trans-4-bromomethylcyclohexyl)-2,4'-difluorobiphenyl was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 22.1 g (0.1 mol) of trans-1-bromomethyl-4-n-propyl-4-silacyclohexane. After a conventional after treatment, purification was conducted by means of chromatography to obtain 37.6 g (yield 81.3%) of 4-(trans-4-(2-(trans-4-n-propyl-4-silacyclohexyl)ethyl)cyclohexyl)-2,4'-difluorobiphenyl.

[Example 92]
Preparation of 4-(trans-4-(2-(trans-4-n-pentyl-4-silacyclohexyl)ethyl)cyclohexyl)-4'-difluoromethoxybiphenyl 27.7 g (0.1 mol) of trans-1-(2-bromoethyl)-4-n-pentyl-4-silacyclohexane was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 88.1 g (0.1 mol) of 4-(4-bromocyclohexyl)-2,4'-difluorobiphenyl. After a conventional after treatment, 4-(trans-4-(2-(trans-4-n-pentyl-4-silacyclohexyl)ethyl)cyclohexyl)-4'-difluoromethoxybiphenyl was obtained. The silacyclohexane rings of the product were a mixture of trans isomers and cis isomers. They were separated by means of chromatography to obtain 11.8 g (yield 25.1%) of the trans isomer.

[Example 93]
Preparation of 4-(trans-4-(2-(trans-4-n-pentyl-4-silacyclohexyl)ethyl)cyclohexyl)-2,4'-difluorobiphenyl 27.7 g (0.1 mol) of trans-1-(2-bromoethyl)-4-n-pentyl-4-silacyclohexane was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 35.1 g (0.1 mol) of 4-(4-bromocyclohexyl)-2,4'-difluorobiphenyl. After a conventional after treatment, 4-(trans-4-(2-(trans-4-n-pentyl-4-silacyclohexyl)ethyl)cyclohexyl)-2,4'-difluorobiphenyl was obtained. The silacyclohexane rings of the product were a mixture of trans isomers and cis isomers. They were separated by means of chromatography to obtain 13.1 g (yield 29.2%) of the trans isomer.

[Example 94]
Preparation of 4-(trans-4-(2-(trans-4-n-pentylcyclohexyl) ethyl)-4-silacyclohexyl)-3',5'-difluoro-4'-trifluoromethoxybiphenyl 26.1 g (0.1 mol) of trans-1-(2-bromoethyl)-4-n-pentylcyclohexane was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 40.7 g (0.1 mol) of 4-(4-chloro-4-silacyclohexyl)3',5'-difluoro-4'-trifluoromethoxybiphenyl. After a conventional after treatment, 4-(2-(trans-4-n-pentylcyclohexyl)ethyl)-4-silacyclohexyl)-3',5'-difluoro-4'-trifluoromethoxybiphenyl was obtained. The silacyclohexane rings of the product were a mixture of trans isomers and cis isomers. They were separated by means of chromatography to obtain 44.3 g (yield 90.1%) of the trans isomer.

[Example 95]
Preparation of 4-(trans-4-(2-(trans-4-n-pentyl-4-silacyclohexyl)ethyl)cyclohexyl)-2,6,3'-trifluoro-4'-difluoromethoxybiphenyl 11.9 g (yield 21.6%) of 4-(trans-4-(2-(trans-4-n-pentyl-4-silacyclohexyl)ethyl)cyclohexyl)-2,6,3'-trifluoro-4'-difluoromethoxybiphenyl was obtained by the same method as Example 92 except for the fact that 43.5 g of 4-(4-bromocyclohexyl)-2,6,3'-trifluoro-4'-difluoromethoxybiphenyl was used instead of the 4-(4-bromocyclohexyl)-2,4'-difluorobiphenyl in Example 94.

[Example 96]
Preparation of 4-(trans-4-(2-(trans-4-n-pentyl-4-silacyclohexyl)ethyl)cyclohexyl)-2,6,3',5'-tetrafluoro-4'-trifluoromethoxybiphenyl 12.2 g (yield 20.7%) of 4-(trans-4-(2-(trans-4-n-pentyl-4-silacyclohexyl)ethyl)cyclohexyl)-2,6,3',5'-tetrafluoro-4'-trifluoromethoxybiphenyl was obtained by the same method as Example 92 except for the fact that 47.1 g of 4-(4-bromocyclohexyl)-2,6,3',5'-tetrafluoro-4'-trifluoromethoxybiphenyl was used instead of the 4-(4-bromocyclohexyl)-2,4'-difluorobiphenyl in Example 92.

[Example 97]
Preparation of 4-(trans-4-(2-(trans-4-n-propyl-4-silacyclohexyl)ethyl)cyclohexyl)-4'-propylbiphenyl 35.7 g (0.1 mol) of 4-(4-bromocyclohexyl)-2,4'-propylbiphenyl was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 24.9 g (0.1 mol) of trans-1-(2-bromoethyl)-4-n-pentyl-4-silacyclohexane. After a conventional after treatment, 4-(trans-4-(2-(trans-4-n-propyl-4-silacyclohexyl)ethyl)cyclohexyl)-4'-propylbiphenyl was obtained. The silacyclohexane rings of the product were a mixture of trans isomers and cis isomers. They were separated by means of chromatography to obtain 34.8 g (yield 77.8%) of the trans isomer.

[Example 98]
Preparation of 4-(trans-4-(2-(trans-4-n-propyl-4-silacyclohexyl)ethyl)cyclohexyl)-2-fluoro-4'-chlorobiphenyl 31.2 g (yield 68.3%) of 4-(trans-4-(2-(trans-4-n-propyl-4-silacyclohexyl)ethyl)cyclohexyl)-2-fluoro-4'-chlorobiphenyl was obtained by the same method as Example 97 except for the fact that 36.8 g of 4-(4-bromocyclohexyl)-2-fluoro-4'-chlorobiphenyl was used instead of the 4-(4-bromocyclohexyl)-2,4'-propylbiphenyl in Example 97.

[Example 99]
Preparation of 4-(trans-4-(2-(trans-4-n-propyl-4-silacyclohexyl)ethyl)cyclohexyl)-3',5'-difluoro-4'-chlorobiphenyl 34.0 g (yield 71.5%) of 4-(trans-4-(2-(trans-4-n-propyl-4-silacyclohexyl)ethyl)cyclohexyl)-3',5'-difluoro-4'-chlorobiphenyl was obtained by the same method as Example 97 except for the fact that 38.6 g of 4-(4-bromocyclohexyl)-3',5'-difluoro-4'-chlorobiphenyl was used instead of the 4-(4-bromocyclohexyl)-2,4'-propylbiphenyl in Example 97.

[Example 100]
Preparation of 4-(trans-4-(2-(trans-4-n-propyl-4-silacyclohexyl)ethyl)cyclohexyl)-2,6,3'-trifluoro-4'-chlorobiphenyl 39.2 g (yield 79.5%) of 4-(trans-4-(2-(trans-4-n-propyl-4-silacyclohexyl)ethyl)cyclohexyl)-2,6,3'-trifluoro-4'-chlorobiphenyl was obtained by the same method as Example 97 except for the fact that 40.4 g of 4-(4-bromocyclohexyl)-2,6,3'-trifluoro-4'-chlorobiphenyl was used instead of the 4-(4-bromocyclohexyl)-2,4'-propylbiphenyl in Example 97.

[Example 101]
Preparation of 4-(trans-4-(2-(trans-4-n-butyl-4-silacyclohexyl)ethyl)cyclohexyl)-2,3',4'-trifluorobiphenyl 36.9 g (0.1 mol) of 4-(4-bromocyclohexyl)-2,3',4'-trifluorobiphenyl was dripped into a mixture of 2.5 g (0.11 mol) of magnesium and 300 ml of THF to obtain a Grignard's reagent. This solution was then dripped into a 500 ml THF solution of 0.5 g of triethyl phosphate, 0.1 g of copper (I) iodide and 26.3 g (0.1 mol) of trans-1-(2-bromoethyl)-4-n-butyl-4-silacyclohexane. After a conventional after treatment, 4-(trans-4-(2-(trans-4-n-butyl-4-silacyclohexyl)ethyl)cyclohexyl)-2,3',4'-trifluorobiphenyl was obtained. The silacyclohexane rings of the product were a mixture of trans isomers and cis isomers. They were separated by means of chromatography to obtain 34.3 g (yield 72.6%) of the trans isomer.

[Example 102]
Preparation of 4-(trans-4-(2-(trans-4-n-pentyl-4-silacyclohexyl)ethyl)cyclohexyl)-2,6,3',5'-tetrafluoro-4'-difluoromethoxybiphenyl 36.0 g (0.1 mol) of 4-(2-(trans-4-n-pentyl-4-silacyclohexyl)ethyl)cyclohexyl bromide was dripped into a mixture of 2.5 g (0.11 mol) of magnesium and 300 ml of THF to obtain a Grignard's reagent. This solution was then dripped into a 500 ml THF solution of 0.5 g of tetrakis triphenylphosphine palladium and 87.1 g (0.1 mol) of 4-bromo-2,6,3',5'-tetrafluoro-4'-difluoromethoxybiphenyl. After a conventional after treatment, 4-(trans-4-(2-(trans-4-n-pentyl-4-silacyclohexyl)ethyl)cyclohexyl)-2,6,3',5'-tetrafluoro-4'-difluoromethoxybiphenyl was obtained. The silacyclohexane rings of the product were a mixture of trans isomers and cis isomers. They were separated by means of chromatography to obtain 40.0 g (yield 70.1%) of the trans isomer.

[Example 103]
Preparation of 4-(trans-4-(2-(trans-4-n-pentyl-4-silacyclohexyl)ethyl)cyclohexyl)-2-fluoro-4'-trifluoromethoxybiphenyl 40.7 g (yield 74.8%) of 4-(trans-4-(2-(trans-4-n-pentyl-4-silacyclohexyl)ethyl)cyclohexyl)-2-fluoro-4'-trifluoromethoxybiphenyl was obtained by the same method as Example 102 except for the fact that 38.2 g of 4-iodo-2-fluoro-4'-trifluoromethoxybiphenyl was used instead of the 4-bromo-2,6,3',5'-tetrafluoro-4'-difluoromethoxybiphenyl in Example 102.

[Example 104]
Preparation of 4-(trans-4-(2-(trans-4-n-pentyl-4-silacyclohexyl)ethyl)cyclohexyl)-3',5'-difluoro-4'-difluoromethoxybiphenyl 33.0 g (yield 61.7%) of 4-(trans-4-(2-(trans-4-n-pentyl-4-silacyclohexyl)ethyl)cyclohexyl)-3',5'-difluoro-4'-difluoromethoxybiphenyl was obtained by the same method as Example 102 except for the fact that 33.5 g of 4-bromo-3',5'-difluoro-4'-difluoromethoxybiphenyl was used instead of the 4-bromo-2,6,3',5'-tetrafluoro-4'-difluoromethoxybiphenyl in Example 102.

[Example 105]
Preparation of 4-(trans-4-(2-(trans-4-n-pentyl-4-silacyclohexyl)ethyl)cyclohexyl)-2,6,3'-trifluoro-4'-trifluoromethoxybiphenyl 45.1 g (yield 79.0%) of 4-(trans-4-(2-(trans-4-n-pentyl-4-silacyclohexyl)ethyl)cyclohexyl)-2,6,3'-trifluoro-4'-trifluoromethoxybiphenyl was obtained by the same method as Example 102 except for the fact that 37.1 g of 4-bromo-2,6,3'-trifluoro-4'-trifluoromethoxybiphenyl was used instead of the 4-bromo-2,6,3',5'-tetrafluoro-4'-difluoromethoxybiphenyl in Example 102.

[Example 106]
Preparation of 4-(trans-4-(2-(trans-4-n-pentyl-4-silacyclohexyl)ethyl)cyclohexyl)-2,6,3',5'-tetrafluoro-4'-trifluoromethoxybiphenyl 36.1 g (yield 61.3%) of 4-(trans-4-(2-(trans-4-n-pentyl-4-silacyclohexyl)ethyl)cyclohexyl)-2,6,3',5'-tetrafluoro-4'-trifluoromethoxybiphenyl was obtained by the same method as Example 102 except for the fact that 38.9 g of 4-bromo-2,6,3',5'-tetrafluoro-4'-trifluoromethoxybiphenyl was used instead of the 4-bromo-2,6,3',5'-tetrafluoro-4'-difluoromethoxybiphenyl in Example 102.

[Example 107]
Preparation of 4-(trans-4-(2-(trans-4-n-pentyl-4-silacyclohexyl)ethyl)cyclohexyl)-3',4'-difluorobiphenyl 26.9 g (0.1 mol) of 4-bromo-3',4'-difluorobiphenyl was dripped into a mixture of 2.5 g (0.11 mol) of magnesium and 300 ml of THF to obtain a Grignard's reagent. This solution was then dripped into a 500 ml THF solution of 0.5 g of copper (I) chloride and 35.9 g (0.1 mol) of 4-(2-(trans-4-n-pentyl-4-silacyclohexyl)ethyl)cyclohexyl bromide. After a conventional after treatment, 4-(trans-4-(2-(trans-4-n-pentyl-4-silacyclohexyl)ethyl)cyclohexyl)-3',4'-difluorobiphenyl was obtained. The silacyclohexane rings of the product were a mixture of trans isomers and cis isomers. They were separated by means of chromatography to obtain 36.0 g (yield 76.9%) of the trans isomer.

[Example 108]
Preparation of 4-(trans-4-(2-(cis-4-methyl-trans-4-n-pentyl-4-silacyclohexyl)ethyl)cyclohexyl)-2,3'-difluoro-4'-chlorobiphenyl 46.3 g (yield 89.5%) of 4-(trans-4-(2-(cis-4-methyl-trans-4-n-pentyl-4-silacyclohexyl)ethyl)cyclohexyl)-2,3'-difluoro-4'-chlorobiphenyl was obtained by the same method as Example 107 except for the fact that 30.4 g of 4-bromo-2,3'-difluoro-4'-chlorobiphenyl was used instead of the 4-bromo-3',4'-difluorobiphenyl in Example 107.

[Example 109]
Preparation of 4-(trans-4-(2-(trans-4-n-pentyl-4-silacyclohexyl)ethyl)cyclohexyl)-3',4',5'-trifluorobiphenyl 37.5 g (yield 77.0%) of 4-(trans-4-(2-(trans-4-n-pentyl-4-silacyclohexyl)ethyl)cyclohexyl)-3',4',5'-trifluorobiphenyl was obtained by the same method as Example 107 except for the fact that 28.7 g of 4-bromo-3',4',5'-trifluorobiphenyl was used instead of the 4-bromo-3',4'-difluorobiphenyl in Example 107.

[Example 110]
Preparation of 4-(trans-4-(2-(trans-4-n-pentyl-4-silacyclohexyl)ethyl)cyclohexyl)-2,6,3'-trifluoro-4'-trifluoromethoxybiphenyl 45.3 g (yield 81.7%) of 4-(trans-4-(2-(trans-4-n-pentyl-4-silacyclohexyl)ethyl)cyclohexyl)-2,6,3'-trifluoro-4'-trifluoromethylbiphenyl was obtained by the same method as Example 107 except for the fact that 85.5 g of 4-bromo-2,6,3'-trifluoro-4'-trifluoromethylbiphenyl was used instead of the 4-bromo-3',4'-difluorobiphenyl in Example 107.

[Example 111]
Preparation of 4-(trans-4-(2-(trans-4-(3-methylbutyl)-4-silacyclohexyl)ethyl)cyclohexyl)-3',4'-difluorobiphenyl 26.9 g (0.1 mol) of 4-bromo-3',4'-difluorobiphenyl was dripped into a mixture of 2.5 g (0.11 mol) of magnesium and 300 ml of THF to obtain a Grignard's reagent. This solution was then dripped into a 500 ml THF solution of 0.5 g of copper (I) chloride and 85.9 g (0.1 mol) of 4-(2-(trans-4-(3-methylbutyl)-4-silacyclohexyl)ethyl)cyclohexyl bromide. After a conventional after treatment, 4-(trans-4-(2-(trans-4-(3-methylbutyl)-4-silacyclohexyl)ethyl)cyclohexyl)-3',4'-difluorobiphenyl was obtained. The silacyclohexane rings of the product were a mixture of trans isomers and cis isomers. They were separated by means of chromatography to obtain 34.2 g (yield 73.0%) of the trans isomer.

[Example 112]
Preparation of 4-(trans-4-(2-(trans-4-n-propyl-4-silacyclohexyl)ethyl)cyclohexyl)-3'-fluoro-4'-cyanobiphenyl 20.9 g (0.1 mol) of 1-bromo-4-chloro-3-fluorobenzene was dripped into a mixture of 2.5 g (0.11 mol) of magnesium and 300 ml of THF to obtain a Grignard's reagent. This solution was then dripped into a 500 ml THF solution of 0.5 g of tetrakis triphenylphosphine palladium and 43.6 g (0.1 mol) of 4-(trans-4-(2-(trans-4-n-propyl-4-silacyclohexyl)ethyl)cyclohexyl)phenyl bromide. After a conventional after treatment, purification was conducted by means of chromatography to obtain 36.4 g (yield 75.1%) of 4-(trans-4-(2-(trans-4-n-propyl-4-silacyclohexyl)ethyl)cyclohexyl)-3'-fluoro-4'-cyanobiphenyl was obtained.

[Example 113]
Preparation of 4-(trans-4-(2-(trans-4-n-propyl-4-silacyclohexyl)ethyl)cyclohexyl)-2,3'-difluoro-4'-trifluoromethoxybiphenyl 25.9 g (0.1 mol) of 1-bromo-3-fluoromethoxybenzene was dripped into a mixture of 2.5 g (0.11 mol) of magnesium and 300 ml of THF to obtain a Grignard's reagent. This solution was then dripped into a 500 ml THF solution of 0.5 g of tetrakis triphenylphosphine palladium and 42.6 g (0.1 mol) of 4-(trans-4-(2-(trans-4-n-propyl-4-silacyclohexyl) ethyl)cyclohexyl)-2-fluorophenyl bromide. After a conventional after treatment, purification was conducted by means of chromatography to obtain 40.2 g (yield 76.6%) of 4-(trans-4-(2-(trans-4-n-propyl-4-silacyclohexyl)ethyl)cyclohexyl)-2,3'-difluoro-4'-trifluoromethoxybiphenyl was obtained.

[Example 114]
Preparation of 4-(trans-4-(2-(trans-4-n-propyl-4-silacyclohexyl)ethyl)cyclohexyl)-2,6,4'-trifluorobiphenyl 17.5 g (0.1 mol) of p-bromochlorobenzene was dripped into a mixture of 2.5 g (0.11 mol) of magnesium and 300 ml of THF to obtain a Grignard's reagent. This was dripped into a 30 ml THF solution of 13.6 g of zinc chloride to obtain an organozinc reagent. This solution was then dripped into a 500 ml THF solution of 0.5 g of tetrakis triphenylphosphine palladium and 49.2 g (0.1 mol) of 4-(trans-4-(2-(trans-4-n-propyl-4-silacyclohexyl)ethyl)cyclohexyl)-2,6-difluorophenyl iodide. After a conventional after treatment, purification was conducted by means of chromatography to obtain 27.2 g (yield 59.4%) of 4-(trans-4-(2-(trans-4-n-propyl-4-silacyclohexyl)ethyl)cyclohexyl) -2,6,4'-trifluorobiphenyl was obtained.

[Example 115]
Preparation of 4-(trans-4-(2-(trans-4-n-propyl-4-silacyclohexyl) ethyl)cyclohexyl)-2,3',4',5'-tetrafluorobiphenyl 21.1 g (0.1 mol) of 1-bromo-3,4,5-trifluorobenzene was dripped into a mixture of 2.5 g (0.11 mol) of magnesium and 300 ml of THF to obtain a Grignard's reagent. This solution was then dripped into a 500 ml THF solution of 0.5 g of tetrakis triphenylphosphine palladium and 47.3 g (0.1 mol) of 4-(trans -4-(2-(trans-4-n-propyl-4-silacyclohexyl)ethyl) cyclohexyl) -2-fluorophenyl iodide. After a conventional after treatment, purification was conducted by means of chromatography to obtain 37.7 g (yield 79.1%) of 4-(trans-4-(2-(trans-4-n-propyl-4-silacyclohexyl)ethyl)cyclohexyl)-2,3',4',5'-tetrafluorobiphenyl was obtained.

[Example 116]
Preparation of 4-(trans-4-(2-(trans-4-(3-methoxypropyl)-4-silacyclohexyl)ethyl)cyclohexyl)-3',4'-difluorobiphenyl 19.3 g (0.1 mol) of 1-bromo-3,4-difluorobenzene was dripped into a mixture of 2.5 g (0.11 mol) of magnesium and 300 ml of THF to obtain a Grignard's reagent. This solution was then dripped into a 500 ml THF solution of 0.5 g of tetrakis triphenylphosphine palladium and 43.8 g (0.1 mol) of 4-(trans-4-(2-(trans-4-(3-methoxypropyl)-4-silacyclohexyl)ethyl)cyclohexyl)phenyl bromide. After a conventional after treatment, purification was conducted by means of chromatography to obtain 28.9 g (yield 61.3%) of 4-(trans-4-(2-(trans-4-(3-methoxypropyl)-4-silacyclohexyl) ethyl)cyclohexyl)-3',4'-difluorobiphenyl was obtained.

[Example 117]
Preparation of 4-(trans-4-(2-(trans-4-n-pentyl-4-silacyclohexyl)ethyl)cyclohexyl)-4'-ethoxybiphenyl 15.7 g (0.1 mol) of p-chloroethoxybenzene was dripped into a mixture of 2.5 g (0.11 mol) of magnesium and 100 ml of THF to obtain a Grignard's reagent. This solution was then dripped into a 100 ml diethyl ether solution of 0.5 g of [1,3-bis(diphenylphosphino)propane]nickel (II) chloride and 31.5 g (0.1 mol) of 4-(trans-4-(2-(trans-4-(3-methoxypropyl)-4-silacyclohexyl)ethyl)cyclohexyl)phenyl chloride. After a conventional after treatment, purification was conducted by means of chromatography to obtain 32.2 g (yield 67.5%) of 4-(trans-4-(2-(trans-4-n-pentyl-4-silacyclohexyl)ethyl)cyclohexyl)-4'-ethoxybiphenyl was obtained.

[Example 118]
A liquid crystal mixture comprising 34% of 2-(trans-4-n-pentylcyclohexyl)-1-(3,4-difluorophenyl)ethane, 15% of 1,2-difluoro-4-[trans-4-(trans-4-n-propylcyclohexyl)cyclohexyl]benzene and 51% of 2-[trans-4-(trans-4-propylcyclohexyl)cyclohexyl]-1-(3,4-difluorophenyl)ethane exhibits the nematic liquid crystal phase in the temperature range of −17° C. to 63° C.

A liquid crystal mixture comprising 85% of this mixture and 15% of trans, trans-4-(4-n-pentyl-4-silacyclohexyl)cyclohexyl)-3',4'-difluorobiphenyl obtained in Example 17 exhibits the nematic liquid crystal phase in the extended temperature range of −22° C. to 88° C.

A liquid crystal mixture comprising 85% of this mixture and 15% of trans, trans-4-(2-(4-(4-n-propyl-4-silacyclohexyl)cyclohexyl)ethyl)-4'-chloro-3'-fluorobiphenyl obtained in Example 48 exhibits the nematic liquid crystal phase in the extended temperature range of −22° C. to 83° C.

We claim:

1. A silacyclohexane compound represented by the following general formula (I):

$$R-\boxed{A}-(CH_2)_{2a}-\boxed{B}-(CH_2)_{2b}-\underset{}{\bigcirc}^{(Y)_i}-\underset{}{\bigcirc}^{(Z)_j}-X \quad (I)$$

wherein R denotes a linear-chain alkyl group with 1–10 carbon atoms, a fluoroalkyl group with 1–10 carbon atoms in which a fluorine atom(s) is substituted for one or two hydrogen atoms, an alkoxy group with 1–10 carbon atoms, a branched-chain alkyl group with 3–8 carbon atoms, an alkoxyalkyl group with 2–7 carbon atoms, or an alkenyl group with 2–8 carbon atoms:

a and b denote 0 or 1 where (a+b) is 0 or 1 at least one of $$-\boxed{A}- \quad \text{and} \quad -\boxed{B}-$$

denotes a trans-1-sila-1,4-cyclohexylene or a trans-4-sila-1,4-cyclohexylene group whose silicon at position 1 or position 4 has a substitutional group(s) of H, F, Cl or $CH_3$, and the other denotes a 1,4-cyclohexylene group, a trans-1-sila-1,4-cyclohexylene or a trans-4-sila-1,4-cyclohexylene group whose silicon at position 1 or position 4 has a substitutional group of H, F, Cl or $CH_3$;

X denotes H, CN, F, Cl, $CF_3$, $CF_2Cl$, $CHFCl$, $OCF_3$, $OCF_2Cl$, $OCHFCl$, $OCHF_2$, R or OR;

Y and Z denotes F, Cl or $CH_3$; and i and j denote 0, 1 or 2.

2. A silacyclohexane compound represented by the following general formula (II):

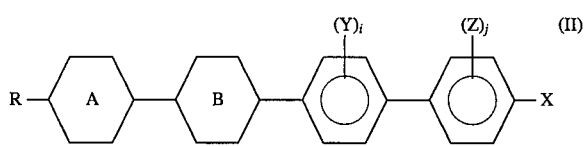

wherein R denotes a linear-chain alkyl group with 1–10 carbon atoms, a fluoroalkyl group with 1–10 carbon atoms in which a fluorine atom(s) is substituted for one or two hydrogen atoms, an alkoxy group with 1–10 carbon atoms, a branched-chain alkyl group with 3–8 carbon atoms, an alkoxyalkyl group with 2–7 carbon atoms, or an alkenyl group with 2–8 carbon atoms:

at least one of

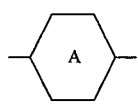

and

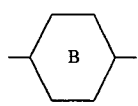

denotes a trans-1-sila-1,4-cyclohexylene or a trans-4-sila-1,4-cyclohexylene group whose silicon at position 1 or position 4 has a substitutional group(s) of H, F, Cl or CH$_3$, and the other denotes a 1,4-cyclohexylene group, a trans-1-sila-1,4-cyclohexylene or a trans-4-sila-1,4-cyclohexylene group whose silicon at position 1 or position 4 has a substitutional group of H, F, Cl or CH$_3$;

X denotes H, CN, F, Cl, CF$_3$, CF$_2$Cl, CHFCl, OCF$_3$, OCF$_2$Cl, OCHFCl, OCHF$_2$, R or OR;

Y and Z denotes F, Cl or CH$_3$; and i and j denote 0, 1 or 2.

3. A silacyclohexane compound represented by the following general formula (III):

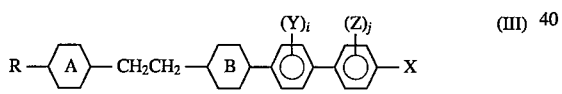

wherein R denotes a linear-chain alkyl group with 1–10 carbon atoms, a fluoroalkyl group with 1–10 carbon atoms in which a fluorine atom(s) is substituted for one or two hydrogen atoms, an alkoxy group with 1–10 carbon atoms, a branched-chain alkyl group with 3–8 carbon atoms, an alkoxyalkyl group with 2–7 carbon atoms, or an alkenyl group with 2–8 carbon atoms:

at least one of

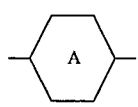

and

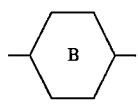

denotes a trans-1-sila-1,4-cyclohexylene or a trans-4-sila-1,4-cyclohexylene group whose silicon at position 1 or position 4 has a substitutional group(s) of H, F, Cl or CH$_3$, and the other denotes a 1,4-cyclohexylene group, a trans-1-sila-1,4-cyclohexylene or a trans-4-sila-1,4-cyclohexylene group whose silicon at position 1 or position 4 has a substitutional group of H, F, Cl or CH$_3$;

X denotes H, CN, F, Cl, CF$_3$, CF$_2$Cl, CHFCl, OCF$_3$, OCF$_2$Cl, OCHFCl, OCHF$_2$, R or OR;

Y and Z denotes F, Cl or CH$_3$; and i and j denote 0, 1 or 2.

4. A silacyclohexane compound represented by the following general formula (IV):

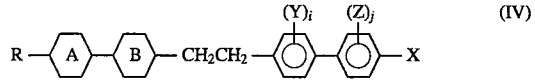

wherein R denotes a linear-chain alkyl group with 1–10 carbon atoms, a fluoroalkyl group with 1–10 carbon atoms in which a fluorine atom(s) is substituted for one or two hydrogen atoms, an alkoxy group with 1–10 carbon atoms, a branched-chain alkyl group with 3–8 carbon atoms, an alkoxyalkyl group with 2–7 carbon atoms, or an alkenyl group with 2–8 carbon atoms:

at least one of

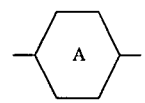

and

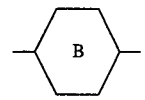

denotes a trans-1-sila-1,4-cyclohexylene or a trans-4-sila-1,4-cyclohexylene group whose silicon at position 1 or position 4 has a substitutional group(s) of H, F, Cl or CH$_3$, and the other denotes a 1,4-cyclohexylene group, a trans-1-sila-1,4-cyclohexylene or a trans-4-sila-1,4-cyclohexylene group whose silicon at position 1 or position 4 has a substitutional group of H, F, Cl or CH$_3$;

X denotes H, CN, F, Cl, CF$_3$, CF$_2$Cl, CHFCl, OCF$_3$, OCF$_2$Cl, OCHFCl, OCHF$_2$, R or OR;

Y and Z denotes F, Cl or CH$_3$; and i and j denote 0, 1 or 2.

5. A method of preparing the silacyclohexane compound as described in claim 1 characterized by the use of a carbon-carbon bond formation reaction or a carbon-silicon bond formation reaction between an organometallic reagent

R—M (M denotes MgP (P denotes a halogen atom), ZnP or Li) and

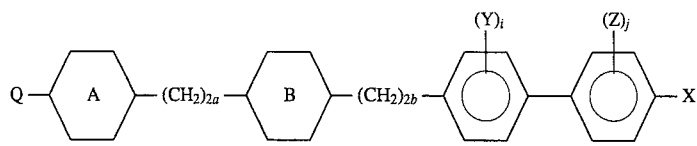

(Q denotes a halogen atom, or an alkoxy having 1–10 carbon atoms, methanesulfonyl, trifluoromethanesulfonyl or p-toluenesulfonyl group).

6. A method of preparing the silacyclohexane compound as described in claim 1 characterized by the use of a carbon-carbon bond formation reaction or a carbon-silicon bond formation reaction between an organometallic reagent

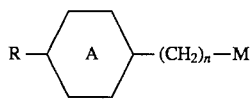

(M denotes MgP (P denotes a halogen atom), ZnP or Li) and

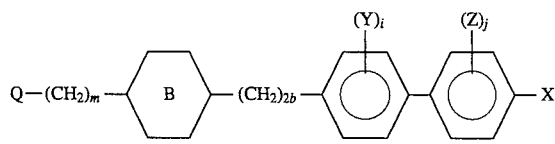

(Q denotes a halogen atom, or an alkoxy having 1–10 carbon atoms, methanesulfonyl, trifluoromethanesulfonyl or p-toluenesulfonyl group, m and n are both the integers 0, 1 or 2, where m+n=2a).

7. A method of preparing the silacyclohexane compound as described in claim 1 characterized by the use of a carbon-carbon bond formation reaction or a carbon-silicon bond formation reaction between an organometallic reagent

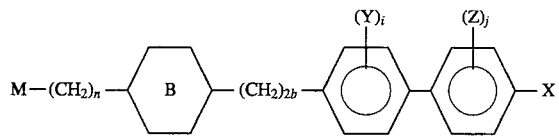

(M denotes MgP (P denotes a halogen atom), ZnP or Li) and

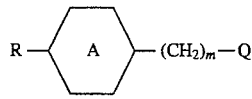

(Q denotes a halogen atom, or an alkoxy having 1–10 carbon atoms, methanesulfonyl, trifluoromethanesulfonyl or p-toluenesulfonyl group, m and n are both the integers 0, 1 or 2, where m+n=2a).

8. A method of preparing the silacyclohexane compound as described in claim 1 characterized by the use of a carbon-carbon bond formation reaction or a carbon-silicon bond formation reaction between an organometallic reagent

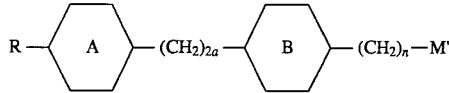

(M' denotes M or B(OY)$_2$, (M denotes MgP (P denotes a halogen atom), ZnP or Li) and Y denotes H or an alkyl group) and

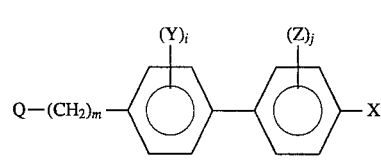

(Q denotes a halogen atom, or an alkoxy having 1–10 carbon atoms, methanesulfonyl, trifluoromethanesulfonyl or p-toluenesulfonyl group, m and n are both integers 0, 1 or 2, where m+n=2b).

9. A method of preparing the silacyclohexane compound as described in claim 1 characterized by the use of a carbon-carbon bond formation reaction or a carbon-silicon bond formation reaction between an organometallic reagent

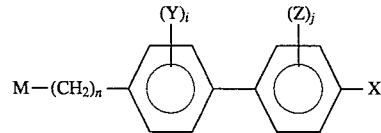

(M denotes MgP (P denotes a halogen atom), ZnP or Li) and

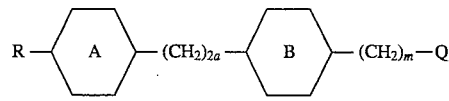

(Q denotes a halogen atom, or an alkoxy having 1–10 carbon atoms, methanesulfonyl, trifluoromethanesulfonyl or p-toluenesulfonyl group, m and n are both the integers 0, 1 or 2, where m+n=2b).

10. A method of preparing the silacyclohexane compound as described in claim 1 characterized by the use of a carbon-carbon bond formation reaction or a carbon-silicon bond formation reaction between an organometallic reagent

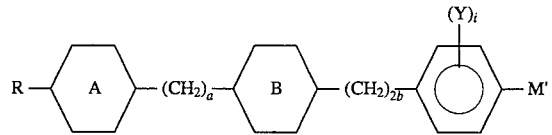

(M' denotes M or B(OY)$_2$, and M denotes MgP (where P denotes a halogen atom) ZnP or Li) and Y denotes H or an alkyl group with 1 or 2 carbon atoms) and

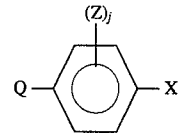

(Q denotes a halogen atom, or an alkoxy having 1–10 carbon atoms, methanesulfonyl, trifluoromethanesulfonyl or p-toluenesulfonyl group).

11. A method of preparing the silacyclohexane compound as described in claim 1 characterized by the use of a carbon-carbon bond formation reaction or a carbon-silicon bond formation reaction between an organometallic reagent

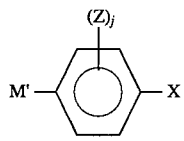

(M' denotes M or $B(OY)_2$, and M denotes MgP (where P denotes a halogen atom) ZnP or Li) and Y denotes H or an alkyl group with 1 or 2 carbon atoms) and

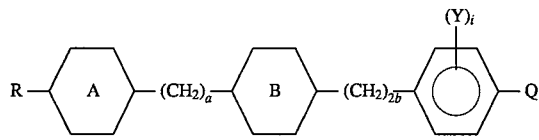

(Q denotes a halogen atom, or an alkoxy having 1–10 carbon atoms, methanesulfonyl, trifluoromethanesulfonyl or p-toluenesulfonyl group).

12. A method of preparing the silacyclohexane compound as described in claim 2 characterized by the use of a carbon-carbon bond formation reaction or a carbon-silicon bond formation reaction between an organometallic reagent

R—M (M denotes MgP (P denotes a halogen atom), ZnP or Li) and

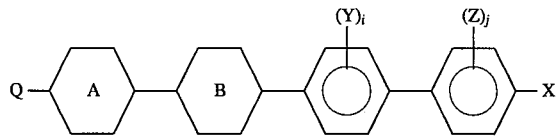

(Q denotes a halogen atom, or an alkoxy having 1–10 carbon atoms, methanesulfonyl, trifluoromethanesulfonyl or p-toluenesulfonyl group).

13. A method of preparing the silacyclohexane compound as described in claim 2 characterized by the use of a carbon-carbon bond formation reaction or a carbon-silicon bond formation reaction between an organometallic reagent

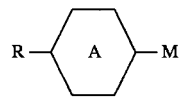

(M denotes MgP (P denotes a halogen atom), ZnP or Li) and

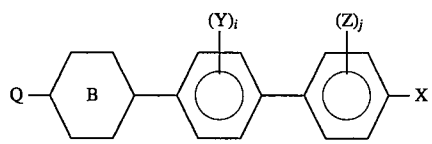

(Q denotes a halogen atom, or an alkoxy having 1–10 carbon atoms, methanesulfonyl, trifluoromethanesulfonyl or p-toluenesulfonyl group).

14. A method of preparing the silacyclohexane compound as described in claim 2 characterized by the use of a carbon-carbon bond formation reaction or a carbon-silicon bond formation reaction between an organometallic reagent

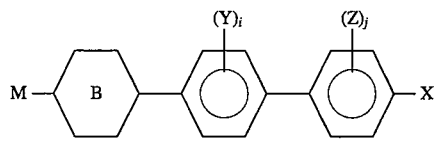

(M denotes MgP (P denotes a halogen atom), ZnP or Li) and

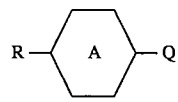

(Q denotes a halogen atom, or an alkoxy having 1–10 carbon atoms, methanesulfonyl, trifluoromethanesulfonyl or p-toluenesulfonyl group).

15. A method of preparing the silacyclohexane compound as described in claim 2 characterized by the use of a carbon-carbon bond formation reaction or a carbon-silicon bond formation reaction between an organometallic reagent

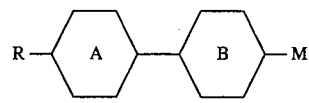

(M denotes MgP (P denotes a halogen atom), ZnP or Li) and

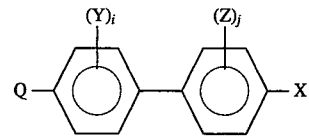

(Q denotes a halogen atom, or an alkoxy having 1–10 carbon atoms, methanesulfonyl, trifluoromethanesulfonyl or p-toluenesulfonyl group).

16. A method of preparing the silacyclohexane compound as described in claim 2 characterized by the use of a carbon-carbon bond formation reaction or a carbon-silicon bond formation reaction between an organometallic reagent

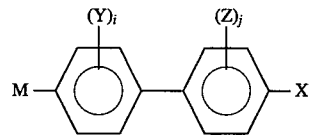

(M denotes MgP (P denotes a halogen atom), ZnP or Li) and

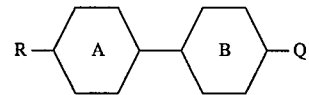

(Q denotes a halogen atom, or an alkoxy having 1–10 carbon atoms, methanesulfonyl, trifluoromethanesulfonyl or p-toluenesulfonyl group).

17. A method of preparing the silacyclohexane compound as described in claim 2 characterized by the use of a carbon-carbon bond formation reaction or a carbon-silicon bond formation reaction between an organometallic reagent

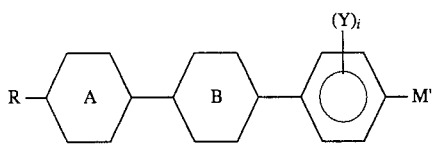

(M' denotes M or B(OY)$_2$ and Y denotes H or an alkyl group with 1 or 2 carbon atoms) and

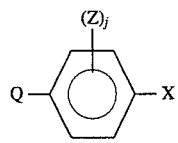

(Q denotes a halogen atom, or an alkoxy having 1–10 carbon atoms, methanesulfonyl, benzenesulfonyl, p-toluenesulfonyl or trifluoromethanesulfonyl).

18. A method of preparing the silacyclohexane compound as described in claim 2 characterized by the use of a carbon-carbon bond formation reaction or a carbon-silicon bond formation reaction between an organometallic reagent

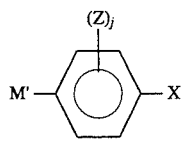

(M' denotes M or B(OY)$_2$ and Y denotes H or an alkyl group with 1 or 2 carbon atoms) and

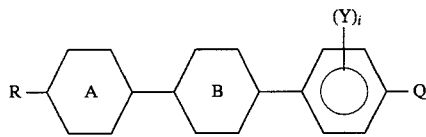

(Q denotes a halogen atom, or an alkoxy having 1–10 carbon atoms, methanesulfonyl, benzenesulfonyl, p-toluenesulfonyl or trifluoromethanesulfonyl).

19. A method of preparing the silacyclohexane compound as described in claim 4 characterized by the use of a carbon-carbon bond formation reaction or a carbon-silicon bond formation reaction between an organometallic reagent

R—M (M denotes MgP (P denotes a halogen atom), ZnP or Li) and

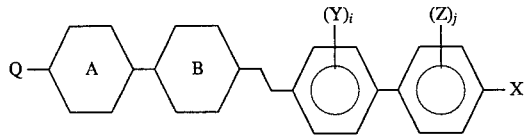

(Q denotes a halogen atom, or an alkoxy having 1–10 carbon atoms, methanesulfonyl, benzenesulfonyl, p-toluenesulfonyl or trifluoromethanesulfonyl group).

20. A method of preparing the silacyclohexane compound as described in claim 4 characterized by the use of a carbon-carbon bond formation reaction or a carbon-silicon bond formation reaction between an organometallic reagent

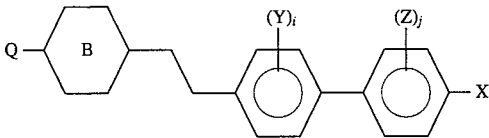

(M denotes MgP (P denotes a halogen atom), ZnP or Li) and

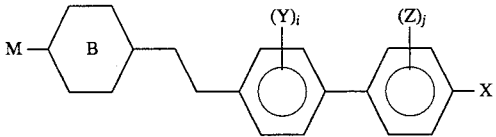

(Q denotes a halogen atom, or an alkoxy having 1–10 carbon atoms, methanesulfonyl, benzenesulfonyl, p-toluenesulfonyl or trifluoromethanesulfonyl group).

21. A method of preparing the silacyclohexane compound as described in claim 4 characterized by the use of a carbon-carbon bond formation reaction or a carbon-silicon bond formation reaction between an organometallic reagent

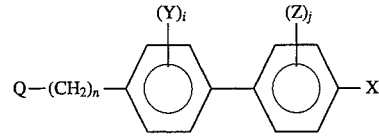

(M denotes MgP (P denotes a halogen atom), ZnP or Li) and

R—⟨A⟩—Q (Q denotes a halogen atom, or an alkoxy having 1–10 carbon atoms, methanesulfonyl, benzenesulfonyl, p-toluenesulfonyl or trifluoromethanesulfonyl group).

22. A method of preparing the silacyclohexane compound as described in claim 4 characterized by the use of a carbon-carbon bond formation reaction between an organometallic reagent R—⟨A⟩—⟨B⟩—(CH$_2$)$_m$—M (M denotes MgP (P denotes a halogen atom), ZnP or Li) and Q—(CH$_2$)$_n$—⟨(Y)$_i$⟩—⟨(Z)$_j$⟩—X (Q denotes a halogen atom, or an alkoxy having 1–10 carbon atoms, methanesulfonyl, benzenesulfonyl, p-toluenesulfonyl or trifluoromethanesulfonyl group, m and n are both the integers 0, 1 or 2, where m+n=2).

23. A method of preparing the silacyclohexane compound as described in claim 4 characterized by the use of a carbon-carbon bond formation reaction or a carbon-silicon bond formation reaction between an organometallic reagent

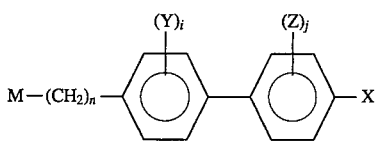

(M denotes MgP (P denotes a halogen atom), ZnP or Li) and

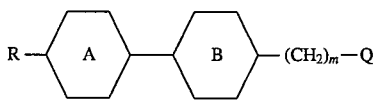

(Q denotes a halogen atom, or an alkoxy having 1–10 carbon atoms, methanesulfonyl, benzenesulfonyl, p-toluenesulfonyl or trifluoromethanesulfonyl group, m and n are both the integers 0, 1 or 2, where m+n=2).

24. A method of preparing the silacyclohexane compound as described in claim 4 characterized by the use of a carbon-carbon bond formation reaction between an organometallic reagent

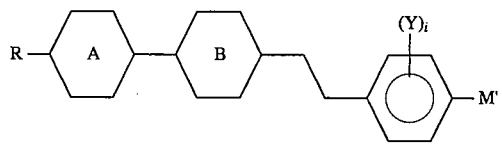

(M' denotes M or B(OR')$_2$ (R' denotes a methyl group or a H atom)) and

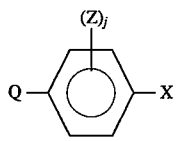

(Q denotes a halogen atom, or an alkoxy having 1–10 carbon atoms, methanesulfonyl, benzenesulfonyl, p-toluenesulfonyl or trifluoromethanesulfonyl group).

25. A method of preparing the silacyclohexane compound as described in claim 4 characterized by the use of a carbon-carbon bond formation reaction between an organometallic reagent

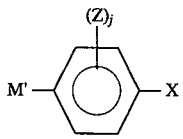

(M' denotes M or B(OR')$_2$ (R' denotes a methyl group or a H atom)) and

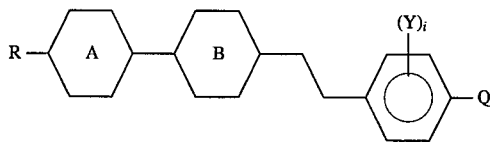

(Q denotes a halogen atom, or an alkoxy having 1–10 carbon atoms, methanesulfonyl, benzenesulfonyl, p-toluenesulfonyl or trifluoromethanesulfonyl group).

26. A method of preparing the silacyclohexane compound as described in claim 3 characterized by the use of a reaction between an organometallic reagent

R—M (M denotes MgP (P denotes a halogen atom), ZnP or Li) and

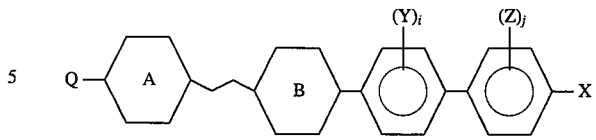

(Q denotes a halogen atom, or an alkoxy having 1–10 carbon atoms, methanesulfonyl, benzenesulfonyl or p-toluenesulfonyl group).

27. A method of preparing the silacyclohexane compound as described in claim 3 characterized by the use of a reaction between an organometallic reagent

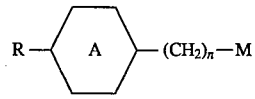

(M denotes MgP (P denotes a halogen atom), ZnP or Li) and

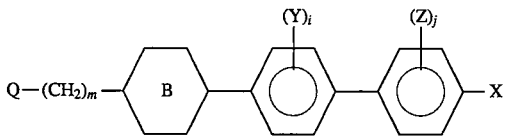

(Q denotes a halogen atom, or an alkoxy having 1–10 carbon atoms, methanesulfonyl, benzenesulfonyl or p-toluenesulfonyl group, n and m are both the integers 0, 1 or 2, where n+m=2).

28. A method of preparing the silacyclohexane compound as described in claim 3 characterized by the use of a reaction between an organometallic reagent

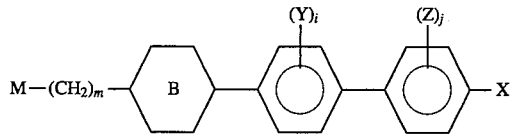

(M denotes MgP (P denotes a halogen atom), ZnP or Li) and

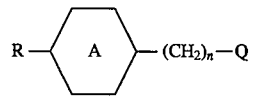

(Q denotes a halogen atom, or an alkoxy having 1–10 carbon atoms, methanesulfonyl, benzenesulfonyl or p-toluenesulfonyl group, n and m are both the integers 0, 1 or 2, where n+m=2).

29. A method of preparing the silacyclohexane compound as described in claim 3 characterized by the use of a reaction between an organometallic reagent

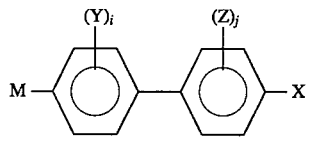

(M denotes MgP (P denotes a halogen atom), ZnP or Li) and

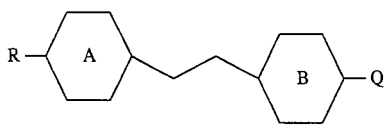

(Q denotes a halogen atom, or an alkoxy having 1–10 carbon atoms, methanesulfonyl, benzenesulfonyl or p-toluenesulfonyl group).

30. A method of preparing the silacyclohexane compound as described in claim 3 characterized by the use of a reaction between an organometallic reagent

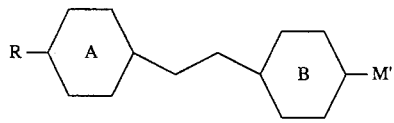

(M' denotes MgP (P denotes a halogen atom), ZnP or B(OY)$_2$ (Y is H or an alkyl group with 1 or 2 carbon atoms) and

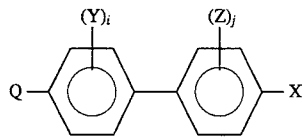

(Q denotes a halogen atom, or an alkoxy having 1–10 carbon atoms, methanesulfonyl, benzenesulfonyl or p-toluenesulfonyl group).

31. A method of preparing the silacyclohexane compound as described in claim 3 characterized by the use of a reaction between an organometallic reagent

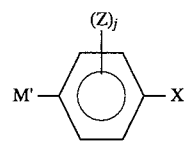

(M' denotes MgP (P denotes a halogen atom), ZnP or B(OY)$_2$ (Y is H or an alkyl group with 1 or 2 carbon atoms) and

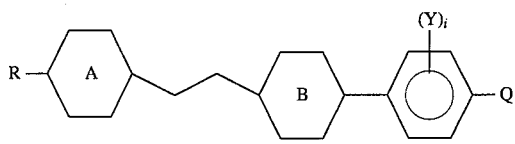

(Q denotes a halogen atom, or an alkoxy having 1–10 carbon atoms, methanesulfonyl, benzenesulfonyl or p-toluenesulfonyl group).

32. A liquid crystal composition comprising the silacyclohexane compound of claim 1.

33. A liquid crystal display element comprising the liquid crystal composition of claim 32.

* * * * *